United States Patent
Sievert et al.

(10) Patent No.: US 9,458,180 B2
(45) Date of Patent: Oct. 4, 2016

(54) METHOD FOR PREPARATION OF CYANO COMPOUNDS OF THE 13TH GROUP WITH A LEWIS ACID

(71) Applicant: Lonza Ltd., Visp (CH)

(72) Inventors: Katharina Sievert, Rostock (DE); Axel Schulz, Rostock (DE); Jorg Harloff, Rostock (DE); Stefan Ellinger, Visp (CH); Christoph Taeschler, Visp (CH); Cornelia Zur Taeschler, Visp (CH)

(73) Assignee: Lonza Ltd., Visp (CH)

( * ) Notice: Subject to any disclaimer, the term of this patent is extended or adjusted under 35 U.S.C. 154(b) by 0 days.

(21) Appl. No.: 15/027,008

(22) PCT Filed: Sep. 23, 2014

(86) PCT No.: PCT/EP2014/070233
§ 371 (c)(1),
(2) Date: Apr. 4, 2016

(87) PCT Pub. No.: WO2015/067405
PCT Pub. Date: May 14, 2015

(65) Prior Publication Data
US 2016/0229874 A1 Aug. 11, 2016

Related U.S. Application Data

(60) Provisional application No. 61/904,748, filed on Nov. 15, 2013.

(30) Foreign Application Priority Data

| Nov. 11, 2013 | (EP) | 13192373 |
| Nov. 15, 2013 | (EP) | 13193107 |
| Feb. 17, 2014 | (EP) | 14155420 |
| May 6, 2014 | (EP) | 14167175 |
| May 21, 2014 | (EP) | 14169209 |
| Jul. 22, 2014 | (EP) | 14177996 |
| Jul. 24, 2014 | (EP) | 14178322 |
| Aug. 5, 2014 | (EP) | 14179786 |
| Aug. 14, 2014 | (EP) | 14181021 |

(51) Int. Cl.
| C07F 5/02 | (2006.01) |
| C07C 209/68 | (2006.01) |
| C07D 233/58 | (2006.01) |
| B01J 27/125 | (2006.01) |
| B01J 29/70 | (2006.01) |
| B01J 31/02 | (2006.01) |

(52) U.S. Cl.
CPC ............. *C07F 5/027* (2013.01); *B01J 27/125* (2013.01); *B01J 29/7049* (2013.01); *B01J 31/0287* (2013.01); *C07C 209/68* (2013.01); *C07D 233/58* (2013.01)

(58) Field of Classification Search
CPC ....................................................... C07F 5/027
See application file for complete search history.

(56) References Cited

U.S. PATENT DOCUMENTS

2011/0150736 A1* 6/2011 Hagiwara ............ C07D 233/58
423/276
2013/0295499 A1 11/2013 Murata et al.

FOREIGN PATENT DOCUMENTS

EP 2327707 6/2011

OTHER PUBLICATIONS

PCT/EP/2014/070233 International Preliminary Report on Patentability, Oct. 9, 2015, 7 pgs.
PCT/EP2014/070233 International Search Report and Written Opinion, Dec. 3, 2014, 11 pgs.
Eduard Bernhardt et al., Die Reaktionen von M|BF$_4$] (M=Li, K) and (C$_2$H$_5$) $_2$O•BF$_3$ mit (CH$_3$)$_3$ SiCN. Bildung von M[BF$_x$(CN)$_4$-X] (M=Li, K; x=1, 2) and (CH$_3$)$_3$(SiNCBF$_x$(CN)$_{3-x}$, (x=0, 1), Zeitschrift Fyur Anorganische Und Allgemeine Chemie, Wiley—V C H Verlag GMBH & Co., KGAA, DE, vol. 629, No. 4, Mar. 1, 2003, pp. 677-685.
Eduard Bernhardt, et al., Eine effiziente Synthese von Tetracyanoboraten durch Sinterprozesse//An Efficient Synthesis for Tetractanobrates by Sinter Processes, Zeitschrift Fur Anorganische Und Allegerneine Chemie, Wiley—V C H Verlag GMBH & Co., KGAA, DE, vol. 629, No. 7/08, Jan. 1, 2003, pp. 1229-1234.
Peter Wasserscheid and Wilheim Keim, Ionische Flüssigkeiten-neue "Lösungen" für die Übergangsmetallkatalyse, AUFSÄTZE, Agnew. Chem 2000, 112, pp. 3926-3945.
John S. Wilkes and Michael J. Zawortko, Air and Water Stable 1-Ethyl-3-methylimidazollum Based Ionic Liquids, J. Chem. Soc., Chem. Commun. 1992, pp. 965-967.
Zieger, et al., "Titanium(IV) Chloride Catalyzed Cyanation of Benzylic Halides With Trimethylsilyl Cyanide", J. Org. Chem., 1994, vol. 59, No. 14, pgs. 3838-3840.

* cited by examiner

*Primary Examiner* — Joseph Kosack
(74) *Attorney, Agent, or Firm* — Dority & Manning, P.A.

(57) ABSTRACT

The invention discloses a method for preparation of cyano compounds of the 13th group of the periodic table with 1, 2, 3 or 4 cyano residues, represented by formula (I): [Cat$^{n+}$] [Z$^1$F$_{4-m}$(CN)$_m$)$^-$]$_n$ by a reaction of [(Z$^1$F$_4$)$^-$] with trimethylsilylcyanide in the presence of a Lewis acid and in the presence of the cation Cat$^{n+}$; Cat$^{2+}$ is a cation, Z$^1$ is B, Al, Ga, In or Tl, m is 1, 2, 3 or 4 and n is 1, 2, 3 or 4.

38 Claims, No Drawings

METHOD FOR PREPARATION OF CYANO COMPOUNDS OF THE 13TH GROUP WITH A LEWIS ACID

RELATED APPLICATIONS

This application is the national stage entry of International Patent Application No. PCT/EP2014/070233 having a filing date of Sep. 23, 2014, which claims the filing benefit of European Patent Application No. 13192373.2, having a filing date of Nov. 11, 2013, European Patent Application No. 13193107.3, having a filing date of Nov. 15, 2013, U.S. Provisional Application No. 61/904,748, having a filing date of Nov. 15, 2013, European Patent Application No. 14155420.4, having a filing date of Feb. 17, 2014, European Patent Application No. 14167175.0, having a filing date of May 6, 2014, European Patent Application No. 14169209.5, having a filing date of May 21, 2014, European Patent Application No. 14177996.7, having a filing date of Jul. 22, 2014, European Patent Application No. 14178322.5, having a filing date of Jul. 24, 2014, European Patent Application No. 14179786.0, having a filing date of Aug. 5, 2014, and European Patent Application No. 14181021.8, having a filing date of Aug. 14, 2014, all of which are incorporated herein by reference in their entirety.

DESCRIPTION

The invention discloses a method for preparation of cyano compounds of the 13th group of the periodic table with 1, 2, 3 or 4 cyano residues, represented by formula (I),

$$[Cat^{n+}][(Z^1F_{4-m}(CN)_m)^-]_n \qquad (I)$$

by a reaction of $[(Z^1F_4)^-]$ with trimethylsilylcyanide in the presence of a Lewis acid and in the presence of the cation $Cat^{n+}$;
$Cat^{n+}$ is a cation, $Z^1$ is B, Al, Ga, In or Tl, m is 1, 2, 3 or 4 and n is 1, 2, 3 or 4.

BACKGROUND OF THE INVENTION

The term "ionic liquid" (IL) is usually used to refer to a salt which is liquid at temperatures below 100° C., in particular at room temperature. Such liquid salts typically comprise organic cations and organic or inorganic anions, and are described inter alia in P. Wasserscheid et al., Angew. Chem., 2000, 112, 3926-3945.

Ionic liquids have a series of interesting properties: Usually, they are thermally stable, relatively non-flammable and have a low vapor pressure. They show good solvability for numerous organic and inorganic substances. In addition, ionic liquids have interesting electrochemical properties, for example electrical conductivity which is often accompanied by a high electrochemical stability.

These attributes give rise to many applications of ionic liquids: They can be used foremost as solvent in synthesis, as electrolyte, as lubricant and as hydraulic fluid. Moreover they serve as phase-transfer catalyst, as extraction medium, as heat-transfer medium, as surface-active substance, as plasticizer, as conductive salt, organic salt or additive in electrochemical cells, as electrolyte, as component in electrolyte formulations, wherein such electrolyte formulation comprising an ionic liquid is preferably used in electrochemical and/or optoelectronic device such as a photovoltaic cell, a light emitting device, an electrochromic or photoelectrochromic device, an electrochemical sensor and/or biosensor, particularly preferred in a dye sensitized solar cell.

Therefore, there is a fundamental need for ionic liquids having a variety of properties which open up additional opportunities for their use.

An interesting family of ionic liquids contains tetravalent boron anions. Tetrafluoroborate containing ionic liquids were among the first of this new generation of compounds and 1-ethyl-3-methylimidazolium tetrafluoroborate ([EMIm][BF$_4$]) was prepared via metathesis of [EMIm]I with Ag[BF$_4$] in methanol as disclosed by J. S. Wilkes et al., J. Chem. Soc. Chem. Commun. 1990, 965.

E. Bernhardt, Z. Anorg. Allg. Chem. 2003, 629, 677-685, discloses the reaction of M[BF$_4$] (M=Li, K) with (CH$_3$)$_3$SiCN (TMSCN). The preparation of Li[BF(CN)$_3$] is disclosed to take 7 days, that of K[BF(CN)$_3$] takes one month. The yield of K[BF(CN)$_3$] was 60%, the product contained 5% K[BF$_2$(CN)$_2$]. The molar ratio of [BF$_4$]$^-$:TMSCN was 1:7.8.

US 2011/150736 A1 discloses as a "Third Production Method" a reaction of three compounds: TMSCN, an amine or ammonium salt, and a boron compound.

EP 2 327 707 A claims in claim 7 a method for producing an ionic compound represented by the general formula (I), comprising a step of reacting starting materials containing a cyanide and a boron compound. General formula (I) is a salt of a cation Kt$^{m+}$ with [B(CN)$_4$]$^-$.

The examples disclose various methods for preparing tetrabutylammonium tetracyanoborate, for example:
1) Example 1-1 of EP 2 327 707 A discloses a reaction of tetrabutylammonium bromide, zinc (II) cyanide and boron tribromide in toluene at 130° C. for 2 days, with a yield of 35%. The molar ratio of boron compound: TMSCN was 1:5.5.
2) Example 2-1 of EP 2 327 707 A discloses a reaction of tetrabutylammonium bromide, tetrabutylammonium cyanide and boron tribromide in toluene at 130° C. for 2 days, with a yield of 77%. The molar ratio of boron compound: tetrabutylammonium cyanide was 1:7.1.
3) Example 3-3 of EP 2 327 707 A discloses a reaction of tetrabutylammonium bromide, trimethylsilyl cyanide and boron trichloride in p-xylene at 150° C. for 30 hours, with a yield of 98%. The molar ratio of boron compound: TMSCN was 1:5.5.
4) Example 3-11 of EP 2 327 707 A discloses a reaction of boron trifluoride diethyl ether, tetrabutylammonium bromide and trimethylsilylcyanide at 170° C. for 30 hours, with a yield of 75%.

But not all embodiments which fall under claim 7 actually work well: Example 3 of the instant invention shows one embodiment also starting with boron trifluoride diethyl ether, which falls under claim 7, but produces the desired [B(CN)$_4$] salt only as a by-product in negligible amounts, the main product is a [BF(CN)$_3$] salt.

There was a need for a simplified method with high yield and satisfactory purity for the preparation of fluoro cyanide compounds of the 13th group of the periodic table with the anion having the general formula [(Z$^1$F$_{4-m}$(CN)$_m$)$^-$] with Z$^1$ is B, Al, Ga, In or Tl and m being 1, 2, 3 or 4. The boron source should be a readily available compound with low costs. The cyanide source should not be a metal cyanide to avoid its negative impact on the environment. The number of reactants should be small and the method should allow the conversion without the presence of a solvent. The content of Cl and Br in the final product should be low. Also the content of Si and cyanide in the final product should be low. The method should require as few steps as possible. The method should allow also the preparation of compounds with m being 1, 2, 3 or 4 and not only of either a compound with m being 3 or a compound with m being 4. The method should avoid the use of $Cl_2$, AgCN or $AgBF_4$. The method should provide stable compounds of said formula which can be used as ionic liquids or as precursors of ionic liquids and can be used e.g. in electrolyte formulations and in electrochemical or optoelectronic devices. These compounds should be able to be disposed of in an environmentally friendly manner after use.

The method should allow the preparation of the desired compounds in high yields and under mild conditions with respect to methods disclosed in the prior art.

This object is achieved by a method using trimethylsilyl-cyanide as CN source and by doing the reaction in the presence of a Lewis acid. No $Cl_2$, AgCN or $AgBF_4$ is required. The content of Cl, Br, Si and cyanide in the final product is low. Another advantage is that the reaction does not require an extra solvent. The method has a reduced number of steps compared to the methods known from the prior art. The method allows for the preparation not only of compounds with m being only 3 or only 4, but for compounds with n being 1, 2, 3 or 4. These compounds can be prepared specifically and individually, and not only as mixtures. The reaction can be done under milder conditions than those used in the methods of the prior art, the reaction can be done at lower temperature or in shorter time.

In this text, the following meanings are used, if not otherwise stated:

alkyl linear or branched alkyl;

$C_{1-q}$ alkyl refers to any alkyl residue which contains from 1 to q carbon atoms; for example $C_{1-6}$ alkyl encompasses inter alia methyl, ethyl, propyl, isopropyl, n-butyl, isobutyl, sec-butyl, tert-butyl, n-pentyl, isopentyl (3-methylbutyl), neopentyl (2,2-dimethylpropyl), n-hexyl and isohexyl (4-methylpentyl);

$C_{2-q}$ alkenyl refers to an alkenyl residue which contains from 2 to q carbon atoms and contains at least one double bond, the carbon chain can be linear or branched; for example $C_{2-4}$ alkenyl encompasses inter alia ethenyl, 1-methylethenyl, prop-1-enyl, prop-2-enyl, 2-methylprop-2-enyl and buta-1,3-dienyl;

$C_{2-q}$ alkynyl refers to an alkynyl residue which contains from 2 to q carbon atoms and contains at least one triple bond, the carbon chain can be linear or branched; for example $C_{2-4}$ alkynyl encompasses inter alia ethynyl, prop-1-ynyl and prop-2-ynyl;

$C_{6-10}$ aryl refers to an aryl residue which has from 6 to 10 carbon atoms and is unsubstituted or substituted by 1, 2, 3 or 4 identical or different substituents independently from each other selected from the group consisting of $C_{1-4}$ alkyl and $C_{1-4}$ alkoxy; for example $C_{6-10}$ aryl encompasses inter alia phenyl, methylphenyl, methoxyphenyl, dimethylphenyl, ethylmethylphenyl, diethylphenyl and naphthyl;

cyclic alkyl or cycloalkyl include cyclo and polycyclo, such as bicyclo or tricyclo, aliphatic residues;

$C_{3-q}$ cycloalkyl refers to a cycloalkyl group having from 3 to q carbon atoms; for example $C_{3-10}$ cycloalkyl encompasses inter alia cyclopropyl, cyclobutyl, cyclopentyl, cyclohexyl, cycloheptyl, cyclooctyl, cyclononyl and cyclodecyl;

$C_{1-q}$ alkoxy refers to an linear or branched alkoxy group having from 1 to q carbon atoms; for example $C_{1-20}$ alkoxy encompasses inter alia methoxy, ethoxy, propoxy, isopropoxy, n-butoxy, isobutoxy, sec-butoxy, tert-butoxy, pentyloxy, 1,4-dimethylpentyloxy, hexyloxy, heptyloxy, octyloxy, 1,5-dimethylhexyloxy, nonyloxy, decyloxy, 4-ethyl-1,5-dimethylhexyloxy, undecyloxy, dodecyloxy, tridecyloxy, tetradecyloxy and eicosyloxy;

alkylene means a linear or branched alkylene group; e.g. propylene, and e.g.

propylene can be connected via its C1 and C2 carbon atoms (a branched alkylene group), or via its C1 and C3 carbon atoms (linear alkylene group);

BMMIm n-Butyl-2-methyl-3-methylimidazolium

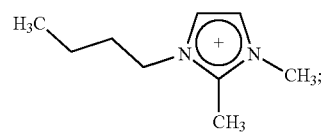

BMPy n-Butylmethylpyridinium

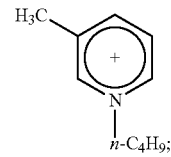

BMPyrr n-Butylmethylpyrrolidinium

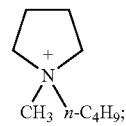

BMPip n-Butylmethylpiperidinium

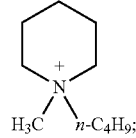

DCM dichloromethane;

EMIm 1-ethyl-3-methylimidazolium

eq. molar equivalent;

halide $F^-$, $Cl^-$, $Br^-$ or $I^-$, preferably $F^-$, $Cl^-$ or $Br^-$, more preferably $Cl^-$;

halogen F, Cl, Br or I; preferably F, Cl or Br;

HEIm 1-ethylimidazolium

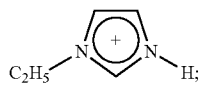

IL ionic liquid;
"linear" and "n-" are used synonymously with respect to the respective isomers of alkanes;
RT room temperature, it is used synonymously with the expression ambient temperature;
$T_{dec}$ decomposition temperature;
THF tetrahydrofuran;
TMSCN $(CH_3)_3SiCN$, i.e. trimethylsilylcyanide;
Trityl means the trityl cation, i.e. $[Ph_3C^+]$
"wt %", "% by weight" and "weight-%" are used synonymously and mean percent by weight.
The expressions dye sensitized solar cell and photosensitized solar cell are used synonymously.

SUMMARY OF THE INVENTION

Subject of the invention is a method for the preparation of compound of formula (I);

$$[Cat^{n+}][(Z^1F_{4-m}(CN)_m)^-]_n \qquad (I)$$

the method comprises a step (St1);
step (St1) comprises a reaction (Rea1), wherein $[(Z^1F_4)^-]$ is reacted with trimethylsilylcyanide in the presence of CATLEWISACID and in the presence of $Cat^{n+}$;
CATLEWISACID is a Lewis Acid selected from the group consisting of Lewis Acid from the 1., 2., 3., 4., 5., 6., 7., 8., 9., 10., 11., 12., 13., 14., 15. and 16. group of the periodic table, zeolite, guanidinium and mixtures thereof;
  $Z^1$ is selected from the group consisting of B, Al, Ga, In and Tl;
  m is 1, 2, 3 or 4;
  n is 1, 2, 3 or 4;
  $Cat^{n+}$ is selected from the group consisting of inorganic cation $CatINORG^{n+}$ and organic cation $CatORG^{n+}$;
  $CatINORG^{n+}$ is a cation selected from the 1., 2., 3., 4., 5., 6., 7., 8., 9., 10., 11., 12., 13., 14., 15. or 16. group of the periodic table, or is a cation from the lanthanides or is a cation from the actinides or is $NH_4^+$;
  $CatORG^{n+}$ is selected from the group consisting of $CatORG-A^+$, $CatORG-B^+$, $CatORG-C^+$, $[(CH_3)_3SiFSi(CH_3)_3]^+$, $Ph_3C^+$, guanidinium and $(H_2(R18)N-R16-N(R19)H_2)^{2+}$;
  $CatORG-A^+$ is $(WR2R3R4R5)^+$,
wherein
  W is a nitrogen or phosphorus; and
  (i) R2, R3, R4 and R5 are identical or different and independently from each other selected from the group consisting of H, $C_{1-20}$ alkyl, $C_{1-20}$ perfluoroalkyl, $C_{3-10}$ cycloalkyl and $C_{6-10}$ aryl, with the proviso, that at least one of the residues R2, R3, R4 and R5 is not H; or
  (ii) R2 and R3 together are a hydrocarbon chain and form together with W a 5- to 7-membered saturated or unsaturated heterocyclic ring,
  R4 and R5 are identical or different and independently from each other selected from the group consisting of H, $C_{1-20}$ alkyl, $C_{1-20}$ perfluoroalkyl, $C_{3-10}$ cycloalkyl and $C_{6-10}$ aryl; or
  (iii) R2 and R3 together are a hydrocarbon chain and form together with W, and R4 and R5 together are a hydrocarbon chain and form together with W, independently from each other, 5- to 7-membered saturated or unsaturated heterocyclic rings;
  $CatORG-B^+$ is $(XR6R7R8)^+$,
wherein
  X is nitrogen,
  R6 and R7 together are a hydrocarbon chain and form together with X a 5- to 7-membered unsaturated heterocyclic ring in which X is connected by a single bond and a double bond to R6 and R7 respectively,
  R8 is selected from the group consisting of H, $C_{1-20}$ alkyl, $C_{2-8}$ alkenyl, $C_{1-20}$ perfluoroalkyl, $C_{3-10}$ cycloalkyl or $C_{6-10}$ aryl;
  $CatORG-C^+$ is $(YR9R10R11)^+$,
wherein
  Y is sulphur;
  R9, R10 and R11 are identical or different and independently from each other selected from the group consisting of H, $C_{1-20}$ alkyl, $C_{1-20}$ perfluoroalkyl, $C_{3-10}$ cycloalkyl and $C_{6-10}$ aryl; or
  (ii) R9 and R10 together are a hydrocarbon chain and form together with Y a 5- to 7-membered saturated or unsaturated ring,
  R11 is selected from the group consisting of H, $C_{1-20}$ alkyl, $C_{1-20}$ perfluoroalkyl, $C_{3-10}$ cycloalkyl and $C_{6-10}$ aryl;
  the residues R2, R3, R4, R5, R6, R7, R8, R9, R10 and R11 are, independently from each other, unsubstituted or, where applicable, substituted by 1, 2, 3, 4, 5 or 6 substituents selected from the group consisting of $C_{1-4}$ alkyl, $C_{3-10}$ cycloalkyl, $C_{2-8}$ alkenyl, phenyl, benzyl, halogen, cyano and $C_{1-4}$ alkoxy;
  in any of said hydrocarbon chains formed by R2 and R3, by R4 and R5, by R6 and R7, by R9 and R10, 1 or 2 carbon atoms of said hydrocarbon chains can be exchanged for 1 or 2 heteroatoms respectively, said one or two heteroatoms being selected from the group consisting of O, N and S; in case of an exchange for N, this N is unsubstituted or substituted by a residue selected from the group consisting of $C_{1-8}$ alkyl, $C_{3-10}$ cycloalkyl, $C_{2-8}$ alkenyl and $C_{1-8}$ perfluoroalkyl;
  R16 is selected from the group consisting of $C_{2-8}$ alkylen, $C_{3-8}$ cycloalkylen, phenylen, C(H)(phenyl), R17(—O—R17)$_{n1}$;
  R17 is selected from the group consisting of $CH_2$—$CH_2$, $CH_2$—$CH_2$—$CH_2$, $CH_2$—$C(H)(CH_3)$—$CH_2$, $CH_2$—$CH_2$—$C(H)(CH_3)$ and $CH_2$—$CH_2$—$CH_2$—$CH_2$;
  R18 and R19 are identical or different and independently from each other selected from the group consisting of H, $C_{1-8}$ alkyl, $C_{3-8}$ cycloalkyl, phenyl and benzyl;
  n1 is an integer from 1 to 20.

DETAILED DESCRIPTION OF THE INVENTION

Preferably, $Z^1$ is B, also in connection with any of the embodiments disclosed in the specification.
Preferably, m is 2, 3 or 4;
more preferably, m is 3 or 4;
also in connection with any of the embodiments disclosed in the specification.
Preferably, n is 1 or 2, also in connection with any of the embodiments disclosed in the specification.
Preferably, CATLEWISACID is selected from the group consisting of $[(CH_3)_3SiFSi(CH_3)_3]^+$, $Q1(R27)_3$, guanidinium, $(R26)_3C^+$, adamantyl cation, $[(R24)_3O]^+$, $[(R25)_3Si]^+$, $Q2(R36)(R28)_3$, $Q3(R29)_3$, $Q4(R30)_5$, Q5(R32)$_3$, Q6(R33)$_2$, Q7(R31), Q8(R34)$_2$, Q9(R35)$_3$, Q10(R37)$_2$, Q11(R38), zeolite and mixtures thereof;

Q1 is selected from the group consisting of B, Al and Ga;

R27 is selected from the group consisting of C$_{1-10}$ alkoxy, halogen, C$_{1-10}$ alkyl, CN, SCN and C$_6$F$_5$;

R24 is C$_{1-10}$ alkyl;

R25 is C$_{1-10}$ alkyl;

R26 is selected from the group consisting of CN, SCN, Ph and C$_{1-10}$ alkyl;

Q2 is selected from the group consisting of Si and Ti;

R28 and R36 are identical or different and independently from each other selected from the group consisting of C$_{1-10}$ alkoxy, halogen, C$_{1-10}$ alkyl, CN, SCN and C$_6$F$_5$;

Q3 is selected from the group consisting of P, Sb and Bi;

R29 is selected from the group consisting of C$_{1-10}$ alkoxy, halogen, CN, SCN, C$_{1-10}$ alkyl and C$_6$F$_5$;

Q4 is selected from the group consisting of P, Sb and Nb;

R30 is selected from the group consisting of C$_{1-10}$ alkoxy, halogen, CN, SCN, C$_{1-10}$ alkyl and C$_6$F$_5$;

Q5 is selected from the group consisting of Cr and Fe;

R32 is selected from the group consisting of halogen, CN and SCN;

Q6 is selected from the group consisting of Mn, Fe, Pd and Pt;

R33 is selected from the group consisting of halogen, CN and SCN;

Q7 is Cu or Ag;

R31 is selected from the group consisting of halogen, CN and SCN;

Q8 is selected from the group consisting of Cu, Zn, Cd and Hg;

R34 is selected from the group consisting of halogen, CN, and SCN;

Q9 Sc or Ln;

R35 is selected from the group consisting of halogen, CN, and SCN;

Q10 Ca;

R37 is halogen;

Q11 K;

R38 is halogen;

more preferably, CATLEWISACID is selected from the group consisting of [(CH3)3SiFSi(CH$_3$)$_3$]$^+$, Si(Cl)(C$_6$H$_5$)$_3$, B(R27)$_3$, Al(R27)$_3$, GaF$_3$, GaCl$_3$, guanidinium, (R26)$_3$C$^+$, [(R24)$_3$O]$^+$, [(R25)$_3$Si]$^+$, Si(R28)$_4$, TiF$_4$, TiCl$_4$, Q3(halogen)$_3$, Q3(CN)$_3$, Q3(C$_{1-4}$ alkyl)$_3$, Q4(halogen)$_5$, Q4(C$_{1-10}$ alkyl)$_5$, Cr(Cl)$_3$, Fe(halogen)$_3$, Mn(Cl)$_2$, Fe(halogen)$_2$, Pd(halogen)$_2$, Pt(halogen)$_2$, Pd(CN)$_2$, Pt(CN)$_2$, Pd(SCN)$_2$, Pt(SCN)$_2$, AgCl, AgCN, CuCl, CuCl$_2$, CuF, CuBr, CuCN, CuF$_2$, CuBr$_2$, Cu(CN)$_2$, ZnF$_2$, ZnCl$_2$, ZnBr$_2$, Zn(CN)$_2$, ScF$_3$, ScCl$_3$, ScBr$_3$, LnF$_3$, LnCl$_3$, LnBr$_3$, CaCl$_2$, KF, zeolite and mixtures thereof;

even more preferably, CATLEWISACID is selected from the group consisting of [(CH3)3SiFSi(CH$_3$)$_3$]$^+$, Si(Cl)(C$_6$H$_5$)$_3$, B(R27)$_3$, Al(R27)$_3$, GaF$_3$, GaCl$_3$, (R26)$_3$C$^+$, [(R24)$_3$O]$^+$, [(R25)$_3$Si]$^+$, Si(halogen)$_4$, Si(C$_{1-10}$ alkyl)$_4$, TiF$_4$, TiCl$_4$, P(halogen)$_3$, P(CN)$_3$, Sb(halogen)$_3$, Bi(halogen)$_3$, Bi(CN)$_3$, P(halogen)$_5$, P(C$_{1-10}$ alkyl)$_5$, Sb(halogen)$_5$, Nb(halogen)$_5$, CrCl$_3$, FeF$_3$, FeCl$_3$, FeBr$_3$, MnCl$_2$, FeF$_2$, FeCl$_2$, FeBr$_2$, PdF$_2$, PdCl$_2$, PdBr$_2$, PtF$_2$, PtCl$_2$, PtBr$_2$, AgCN, CuCl, CuCl$_2$, CuF, CuBr, CuCN, CuF$_2$, ZnF$_2$, ZnCl$_2$, ZnBr$_2$, Zn(CN)$_2$, ScF$_3$, ScCl$_3$, LnF$_3$, LnCl$_3$, CaCl$_2$, KF, zeolite and mixtures thereof;

especially, CATLEWISACID is selected from the group consisting of [(CH$_3$)$_3$SiFSi(CH$_3$)$_3$]$^+$, Si(Cl)(C$_6$H$_5$)$_3$, BF$_3$, BCl$_3$, BBr$_3$, B(C$_{1-4}$ alkyl)$_3$, B(C$_6$F$_5$)$_3$, AlF$_3$, AlCl$_3$, Al(C$_{1-4}$ alkyl)$_3$, Al(C$_6$F$_5$)$_3$, GaF$_3$, GaCl$_3$, (Ph)$_3$C$^+$, (CH$_3$)$_3$C$^+$, [(C$_{1-3}$ alkyl)$_3$O]$^+$, [(C$_{1-4}$ alkyl)$_3$Si]$^+$, Si(halogen)$_4$, Si(C$_{1-10}$ alkyl)$_4$, TiF$_4$, TiCl$_4$, P(halogen)$_3$, P(CN)$_3$, SbF$_3$, SbI$_3$, BiF$_3$, BiI$_3$, Bi(CN)$_3$, P(halogen)$_5$, SbF$_5$, NbF$_5$, NbCl$_5$, CrCl$_3$, FeCl$_3$, FeBr$_3$, MnCl$_2$, FeCl$_2$, FeBr$_2$, PdCl$_2$, PdBr$_2$, PtCl$_2$, PtBr$_2$, AgCN, CuCl, CuCl$_2$, CuF, CuF$_2$, ZnF$_2$, ZnCl$_2$, ZnBr$_2$, Zn(CN)$_2$, ScF$_3$, ScCl$_3$, LnF$_3$, LnCl$_3$, CaCl$_2$, KF, zeolite and mixtures thereof;

more especially, CATLEWISACID is selected from the group consisting of [(CH$_3$)$_3$SiFSi(CH$_3$)$_3$]$^{30}$, Si(Cl)(C$_6$H$_5$)$_3$, BF$_3$, BCl$_3$, B(C$_{1-4}$ alkyl)$_3$, B(C$_6$F$_5$)$_3$, AlCl$_3$, GaF$_3$, GaCl$_3$, (Ph)$_3$C$^+$, (CH$_3$)$_3$C$^+$, [(C$_{1-4}$ alkyl)$_3$Si]$^+$, SiF$_4$, SiCl$_4$, Si(C$_{1-8}$ alkyl)$_4$, TiF$_4$, TiCl$_4$, PCl$_3$, PBr$_3$, PI$_3$, P(CN)$_3$, SbF$_3$, SbI$_3$, Bi(CN)$_3$, PF$_5$, PCl$_5$, PBr$_5$, PI$_5$, SbF$_5$, NbCl$_5$, CrCl$_3$, FeCl$_3$, FeBr$_3$, MnCl$_2$, FeCl$_2$, FeBr$_2$, PdCl$_2$, PdBr$_2$, PtCl$_2$, PtBr$_2$, AgCN, CuCl, CuCl$_2$, CuF, CuF$_2$, ZnF$_2$, Zn(CN)$_2$, ScF$_3$, ScCl$_3$, LnF$_3$, LnCl$_3$, CaCl$_2$, KF, zeolite and mixtures thereof;

even more especially, CATLEWISACID is selected from the group consisting of [(CH3)3SiFSi(CH$_3$)$_3$]$^+$, Si(Cl)(C$_6$H$_5$)$_3$, BF$_3$, BCl$_3$, B(C$_6$F$_5$)$_3$, AlCl$_3$, GaF$_3$, GaCl$_3$, Ph$_3$C$^+$, [(C$_{1-4}$ alkyl)$_3$Si]$^+$, SiF$_4$, SiCl$_4$, Si(C$_{1-4}$ alkyl)$_4$, TiF$_4$, TiCl$_4$, PCl$_3$, PBr$_3$, PI$_3$, P(CN)$_3$, SbF$_3$, SbI$_3$, Bi(CN)$_3$, PF$_5$, PCl$_5$, PBr$_5$, PI$_5$, SbF$_5$, NbCl$_5$, CrCl$_3$, FeCl$_3$, FeBr$_3$, MnCl$_2$, FeCl$_2$, FeBr$_2$, PdCl$_2$, PdBr$_2$, PtCl$_2$, PtBr$_2$, AgCN, CuCl, CuCl$_2$, CuF, CuF$_2$, ZnF$_2$, ScF$_3$, ScCl$_3$, LnF$_3$, LnCl$_3$, CaCl$_2$, KF, zeolite and mixtures thereof;

in particular, CATLEWISACID is selected from the group consisting of [(CH3)3SiFSi(CH$_3$)$_3$]$^+$, Si(Cl)(C$_6$H$_5$)$_3$, BF$_3$, BCl$_3$, B(C$_6$F$_5$)$_3$, AlCl$_3$, GaF$_3$, GaCl$_3$, Ph$_3$C$^+$, [(ethyl)$_3$Si]$^+$, SiCl$_4$, TiF$_4$, TiCl$_4$, P(CN)$_3$, SbF$_3$, Bi(CN)$_3$, PF$_5$, PCl$_5$, SbF$_5$, NbCl$_5$, CrCl$_3$, FeCl$_3$, MnCl$_2$, AgCN, CuCl, CuCl$_2$, ZnF$_2$, CaCl$_2$, KF, zeolite and mixtures thereof;

more in particular, CATLEWISACID is selected from the group consisting of [(CH3)3SiFSi(CH$_3$)$_3$]$^+$, Si(Cl)(C$_6$H$_5$)$_3$, BF$_3$, GaF$_3$, GaCl$_3$, [(ethyl)$_3$Si]$^+$, Ph$_3$C$^+$, SiCl$_4$, TiF$_4$, TiCl$_4$, P(CN)$_3$, PF$_5$, PCl$_5$, SbF$_5$, NbCl$_5$, CrCl$_3$, FeCl$_3$, MnCl$_2$, AgCN, CaCl$_2$, KF, SiCl$_4$, zeolite and mixtures thereof;

even more in particular, CATLEWISACID is selected from the group consisting of [(CH$_3$)$_3$SiFSi(CH$_3$)$_3$]$^+$, Si(Cl)(C$_6$H$_5$)$_3$, BF$_3$, GaF$_3$, GaCl$_3$, [(ethyl)$_3$Si]$^+$, Ph$_3$C$^+$, SiCl$_4$, TiF$_4$, TiCl$_4$, P(CN)$_3$, PF$_5$, PCl$_5$, SbF$_5$, NbCl$_5$, CrCl$_3$, FeCl$_3$, MnCl$_2$, SiCl$_4$, zeolite and mixtures thereof;

in a very preferred embodiment, CATLEWISACID is selected from the group consisting of B(F)$_3$, GaF$_3$, GaCl$_3$, [(ethyl)$_3$Si]$^+$, Pn$_3$C$^+$, TiF$_4$, TiCl$_4$, PF$_5$, PCl$_5$, [(C$_{1-4}$ alkyl)$_3$Si]$^+$, [(CH$_3$)$_3$SiFSi(CH$_3$)$_3$]$^+$, Sb(F)$_5$, zeolite and mixtures thereof;

in a more very preferred embodiment, CATLEWISACID is [(CH$_3$)$_3$SiFSi(CH$_3$)$_3$]$^+$, GaF$_3$, GaCl$_3$, [(ethyl)$_3$Si]$^+$, Ph$_3$C$^+$, TiF$_4$, TiCl$_4$, PF$_5$, PCl$_5$, zeolite or mixtures thereof;

in an even more very preferred embodiment, CATLEWISACID is [(CH$_3$)$_3$SiFSi(CH$_3$)$_3$]$^+$, GaF$_3$, GaCl$_3$, Ph$_3$C$^+$, TiF$_4$, TiCl$_4$, PF$_5$, PCl$_5$, zeolite or mixtures thereof;

in an especially very preferred embodiment, CATLEWISACID is GaF$_3$, GaCl$_3$, Ph$_3$C$^+$, TiF$_4$, TiCl$_4$, PF$_5$, PCl$_5$, zeolite or mixtures thereof.

Preferably,
Q1 is B.
Preferably,
R24 is $C_{1-4}$ alkyl;
R25 is $C_{1-7}$ alkyl;
R26 is selected from the group consisting of Ph and $C_{1-4}$ alkyl;
R27 is selected from the group consisting of $C_{1-7}$ alkoxy, Cl, F, Br, $C_{1-7}$ alkyl and $C_6F_5$;
more preferably,
R24 is $C_{1-3}$ alkyl;
R25 is $C_{1-5}$ alkyl;
R26 is selected from the group consisting of Ph and $C_{1-2}$ alkyl;
R27 is selected from the group consisting of $C_{1-4}$ alkoxy, Cl, F, $C_{1-4}$ alkyl and $C_6F_5$;
even more preferably,
R24 is methyl or ethyl;
R25 is $C_{1-4}$ alkyl;
R26 is Ph or methyl;
R27 is selected from the group consisting of $C_{1-3}$ alkoxy, Cl, F, $C_{1-3}$ alkyl and $C_6F_5$.
In another preferred embodiment, CATLEWISACID is selected from the group consisting of [(CH3)3SiFSi$(CH_3)_3$]$^+$, $Ph_3C^+$, $B(C_6F_5)_3$, and mixtures thereof;
more preferably, CATLEWISACID is $Ph_3C$.
Preferably, CATLEWISACID is used in the reaction (Rea1) in form of a catalyst CAT;
CAT is a Lewis Acid selected from the group consisting of Lewis Acid from the 1., 2., 3., 4., 5., 6., 7., 8., 9., 10., 11., 12., 13., 14., 15. and 16. group of the periodic table, zeolite, guanidinium[ANIO] and mixtures thereof;
more preferably, CAT is selected from the group consisting of [$(CH_3)_3SiFSi(CH_3)_3$][ANIO], Q1$(R27)_3$, guanidinium[ANIO], $(R26)_3C$[ANIO], adamantyl[ANIO], [$(R24)_3O$][ANIO], [$(R25)_3Si$][ANIO], Q2$(R36)(R28)_3$, Q3$(R29)_3$, Q4$(R30)_5$, Q5$(R32)_3$, Q6$(R33)_2$, Q7(R31), Q8$(R34)_2$, Q9$(R35)_3$, Q10$(R37)_2$, Q11(R38), zeolite and mixtures thereof;
even more preferably, CAT is selected from the group consisting of [$(CH_3)_3SiFSi(CH_3)_3$][ANIO], Si(Cl)$(C_6H_5)_3$, B$(R27)_3$, Al$(R27)_3$, $GaF_3$, $GaCl_3$, guanidinium[ANIO], $(R26)_3C$[ANIO], [$(R24)_3O$][ANIO], [$(R25)_3Si$][ANIO], Si$(R28)_4$, $TiF_4$, $TiCl_4$, Q3(halogen)$_3$, Q3$(CN)_3$, Q3$(C_{1-4}$ alkyl$)_3$, Q4(halogen)$_5$, Q4$(C_{1-10}$ alkyl$)_5$, Cr(Cl)$_3$, Fe(halogen)$_3$, Mn$(Cl)_2$, Fe(halogen)$_2$, Pd(halogen)$_2$, Pt(halogen)$_2$, Pd$(CN)_2$, Pt$(CN)_2$, Pd$(SCN)_2$, Pt$(SCN)_2$, AgCl, AgCN, CuCl, $CuCl_2$, CuF, CuBr, CuCN, $CuF_2$, $CuBr_2$, Cu$(CN)_2$, $ZnF_2$, $ZnCl_2$, $ZnBr_2$, Zn$(CN)_2$, $ScF_3$, $ScCl_3$, $ScBr_3$, $LnF_3$, $LnCl_3$, $LnBr_3$, $CaCl_2$, KF, zeolite and mixtures thereof;
especially, CAT is selected from the group consisting of [$(CH_3)_3SiFSi(CH_3)_3$][ANIO], Si(Cl)$(C_6H_5)_3$, B$(R27)_3$, Al$(R27)_3$, $GaF_3$, $GaCl_3$, $(R26)_3C$[ANIO], [$(R24)_3O$][ANIO], [$(R25)_3Si$][ANIO], Si(halogen)$_4$, Si$(C_{1-10}$ alkyl$)_4$, $TiF_4$, $TiCl_4$, P(halogen)$_3$, P$(CN)_3$, Sb(halogen)$_3$, Bi(halogen)$_3$, Bi$(CN)_3$, P(halogen)$_5$, P$(C_{1-10}$ alkyl$)_5$, Sb(halogen)$_5$, Nb(halogen)$_5$, $CrCl_3$, $FeF_3$, $FeCl_3$, $FeBr_3$, $MnCl_2$, $FeF_2$, $FeCl_2$, $FeBr_2$, $PdF_2$, $PdCl_2$, $PdBr_2$, $PtF_2$, $PtCl_2$, $PtBr_2$, AgCN, CuCl, $CuCl_2$, CuF, CuBr, CuCN, $CuF_2$, $ZnF_2$, $ZnCl_2$, $ZnBr_2$, Zn$(CN)_2$, $ScF_3$, $ScCl_3$, $LnF_3$, $LnCl_3$, $CaCl_2$, KF, zeolite and mixtures thereof;
more especially, CAT is selected from the group consisting of [$(CH_3)_3SiFSi(CH_3)_3$][ANIO], Si(Cl)$(C_6H_5)_3$, $BF_3$, $BCl_3$, $BBr_3$, B$(C_{1-4}$ alkyl$)_3$, B$(C_6F_5)_3$, $AlF_3$, $AlCl_3$, Al$(C_{1-4}$ alkyl$)_3$, Al$(C_6F_5)_3$, $GaF_3$, $GaCl_3$, $(Ph)_3C$[ANIO], $(CH_3)_3C$[ANIO], [$(C_{1-3}$ alkyl$)_3O$][ANIO], [$(C_{1-4}$ alkyl$)_3Si$][ANIO], Si(halogen)$_4$, Si$(C_{1-10}$ alkyl$)_4$, $TiF_4$, $TiCl_4$, P(halogen)$_3$, P$(CN)_3$, $SbF_3$, $SbI_3$, $BiF_3$, $BiI_3$, Bi$(CN)_3$, P(halogen)$_5$, $SbF_5$, $NbF_5$, $NbCl_5$, $CrCl_5$, $FeCl_3$, $FeBr_3$, $MnCl_2$, $FeCl_2$, $FeBr_2$, $PdCl_2$, $PdBr_2$, $PtCl_2$, $PtBr_2$, AgCN, CuCl, $CuCl_2$, CuF, $CuF_2$, $ZnF_2$, $ZnCl_2$, $ZnBr_2$, Zn$(CN)_2$, $ScF_3$, $ScCl_3$, $LnF_3$, $LnCl_3$, $CaCl_2$, KF, zeolite and mixtures thereof;
even more especially, CAT is selected from the group consisting of [$(CH_3)_3SiFSi(CH_3)_3$][ANIO], Si(Cl)$(C_6H_5)_3$, $BF_3$, $BCl_3$, B$(C_{1-4}$ alkyl$)_3$, B$(C_6F_5)_3$, $AlCl_3$, $GaF_3$, $GaCl_3$, $(Ph)_3C$[ANIO], $(CH_3)_3C$[ANIO], [$(C_{1-4}$ alkyl$)_3Si$][ANIO], $SiF_4$, $SiCl_4$, Si$(C_{1-8}$ alkyl$)_4$, $TiF_4$, $TiCl_4$, $PCl_3$, $PBr_3$, $PI_3$, P$(CN)_3$, $SbF_3$, $SbI_3$, Bi$(CN)_3$, $PF_5$, $PCl_5$, $PBr_5$, $PI_5$, $SbF_5$, $NbCl_5$, $CrCl_3$, $FeCl_3$, $FeBr_3$, $MnCl_2$, $FeCl_2$, $FeBr_2$, $PdCl_2$, $PdBr_2$, $PtCl_2$, $PtBr_2$, AgCN, CuCl, $CuCl_2$, CuF, $CuF_2$, $ZnF_2$, Zn$(CN)_2$, $ScF_3$, $ScCl_3$, $LnF_3$, $LnCl_3$, $CaCl_2$, KF, zeolite and mixtures thereof;
in particular, CAT is selected from the group consisting of [$(CH_3)_3SiFSi(CH_3)_3$][ANIO], Si(Cl)$(C_6H_5)_3$, $BF_3$, $BCl_3$, B$(C_6F_5)_3$, $AlCl_3$, $GaF_3$, $GaCl_3$, $Ph_3C$[ANIO], [$(C_{1-4}$ alkyl$)_3Si$][ANIO], $SiF_4$, $SiCl_4$, Si$(C_{1-4}$ alkyl$)_4$, $TiF_4$, $TiCl_4$, $PCl_3$, $PBr_3$, $PI_3$, P$(CN)_3$, $SbF_3$, $SbI_3$, Bi$(CN)_3$, $PF_5$, $PCl_5$, $PBr_5$, $PI_5$, $SbF_5$, $NbCl_5$, $CrCl_3$, $FeCl_3$, $FeBr_3$, $MnCl_2$, $FeCl_2$, $FeBr_2$, $PdCl_2$, $PdBr_2$, $PtCl_2$, $PtBr_2$, AgCN, CuCl, $CuCl_2$, CuF, $CuF_2$, $ZnF_2$, $ScF_3$, $ScCl_3$, $LnF_3$, $LnCl_3$, $CaCl_2$, KF, zeolite and mixtures thereof;
more in particular, CAT is selected from the group consisting of [$(CH_3)_3SiFSi(CH_3)_3$][ANIO], Si(Cl)$(C_6H_5)_3$, $BF_3$, $BCl_3$, B$(C_6F_5)_3$, $AlCl_3$, $GaF_3$, $GaCl_3$, $Ph_3C$[ANIO], $SiCl_4$, $TiF_4$, $TiCl_4$, P$(CN)_3$, $SbF_3$, Bi$(CN)_3$, $PF_5$, $PCl_5$, $SbF_5$, $NbCl_5$, $CrCl_3$, $FeCl_3$, $MnCl_2$, AgCN, CuCl, $CuCl_2$, $ZnF_2$, $CaCl_2$, KF, zeolite and mixtures thereof;
even more in particular, CAT is selected from the group consisting of [$(CH_3)_3SiFSi(CH_3)_3$][ANIO], Si(Cl)$(C_6H_5)_3$, $BF_3$, B$(C_6F_5)_3$, $GaF_3$, $GaCl_3$, $Ph_3C$[ANIO], $SiCl_4$, $TiF_4$, $TiCl_4$, P$(CN)_3$, $PF_5$, $PCl_5$, $SbF_5$, $NbCl_5$, $CrCl_3$, $FeCl_3$, $MnCl_2$, AgCN, $CaCl_2$, KF, $SiCl_4$, zeolite and mixtures thereof;
very even more in particular, CAT is selected from the group consisting of [$(CH_3)_3SiFSi(CH_3)_3$][ANIO], Si(Cl)$(C_6H_5)_3$, $BF_3$, B$(C_6F_5)_3$, $GaF_3$, $GaCl_3$, $Ph_3C$[ANIO], $SiCl_4$, $TiF_4$, $TiCl_4$, P$(CN)_3$, $PF_5$, $PCl_5$, $SbF_5$, $NbCl_5$, $CrCl_3$, $FeCl_3$, $MnCl_2$, $SiCl_4$, zeolite and mixtures thereof;
in a very preferred embodiment, CAT is selected from the group consisting of $BF_3$, B$(C_6F_5)_3$, $GaF_3$, $GaCl_3$, $TiF_4$, $TiCl_4$, $PF_5$, $PCl_5$, [$(CH_3)_3SiFSi(CH_3)_3$][ANIO], $Ph_3C$[ANIO], Sb$(F)_5$, zeolite and mixtures thereof;
in a more very preferred embodiment, CAT is [$(CH_3)_3SiFSi(CH_3)_3$][ANIO], B$(C_6F_5)_3$, $GaF_3$, $GaCl_3$, $TiF_4$, $TiCl_4$, $PF_5$, $PCl_5$, $Ph_3C$[ANIO], zeolite or mixtures thereof;
in an even more very preferred embodiment, CAT is [$(CH_3)_3SiFSi(CH_3)_3$][ANIO], B$(C_6F_5)_3$, $GaF_3$, $GaCl_3$, $TiF_4$, $TiCl_4$, $PF_5$, $PCl_5$, $Ph_3C$[ANIO], zeolite or mixtures thereof;
in an especially very preferred embodiment, CAT is B$(C_6F_5)_3$, $GaF_3$, $GaCl_3$, $TiF_4$, $TiCl_4$, $PF_5$, $PCl_5$, $Ph_3C$[ANIO], zeolite or mixtures thereof;
ANIO is selected from the group consisting of [P$(R40)_{6-m1}$ $(R41)_{m1}$]$^-$, [B$(R42)_{4-m2}$$(R43)_{m2}$]$^-$, $F^-$, $Cl^-$, $Br^-$, $I^-$, $CN^-$ and $SCN^-$;

R40 and R41 are identical of different in independently from each other selected from the group consisting of CN, SCN, F, Cl, Br and I;

m1 is 0, 1, 2, 3, 4 or 5;

R42 and R43 are identical of different in independently from each other selected from the group consisting of $C_6F_5$, CN, SCN, F, Cl, Br and I;

m2 is 0, 1, 2 or 3;

preferably, ANIO is selected from the group consisting of $P(R40)_6^-$, $B(R42)_4^-$, $F^-$, $Cl^-$, $Br^-$, $I^-$, $CN^-$ and $SCN^-$;

R40 is selected from the group consisting of CN, SCN, F, Cl, Br and I;

R42 is selected from the group consisting of $C_6F_5$, CN, SCN, F, Cl, Br and I;

more preferably, ANIO is selected from the group consisting of $P(R40)_6^-$, $B(R42)_4^-$, $F^-$, $Cl^-$, $Br^-$, $CN^-$ and $SCN^-$;

R40 is selected from the group consisting of CN, SCN, F, Cl and Br;

R42 is selected from the group consisting of $C_6F_5$, CN, SCN, F, Cl and Br;

with Q1, R27, R24, R25, R26, Q2, R28, R36, Q3, R29, Q4, R30, Q5, R32, Q6, R33, Q7, R31, Q8, R34, Q9, R35, Q10, R37, Q11 and R38 as defined herein, also with all their embodiments.

Preferably, [ANIO] is $[B(C_6F_5)_4]$ or $[BF_4]$.

Special embodiments of CAT are $[(CH_3)_3SiFSi(CH_3)_3][B(C_6F_5)_4]$, $Si(Cl)(C_6H_5)_3$, $BF_3$, $B(C_6F_5)_3$, $GaF_3$, $GaCl_3$, $Ph_3C[BF_4]$, $SiCl_4$, $TiF_4$, $TiCl_4$, $P(CN)_3$, $PF_5$, $PCl_5$, $SbF_5$, $NbCl_5$, $CrCl_3$, $FeCl_3$, $MnCl_2$, AgCN, $CaCl_2$, KF, $SiCl_4$, zeolite and mixtures thereof;

very even more in particular, CAT is selected from the group consisting of $[(CH_3)_3SiFSi(CH_3)_3][B(C_6F_5)_4]$, $Si(Cl)(C_6H_5)_3$, $BF_3$, $B(C_6F_5)_3$, $GaF_3$, $GaCl_3$, $Ph_3C[BF_4]$, $SiCl_4$, $TiF_4$, $TiCl_4$, $P(CN)_3$, $PF_5$, $PCl_5$, $SbF_5$, $NbCl_5$, $CrCl_3$, $FeCl_3$, $MnCl_2$, $SiCl_4$, zeolite and mixtures thereof;

in a very preferred embodiment, CAT is selected from the group consisting of $[(CH_3)_3SiFSi(CH_3)_3][B(C_6F_5)_4]$, $BF_3$, $B(C_6F_5)_3$, $GaF_3$, $GaCl_3$, $TiF_4$, $TiCl_4$, $PF_5$, $PCl_5$, $Sb(F)_5$, zeolite and mixtures thereof;

in a more very preferred embodiment, CAT is $[(CH_3)_3SiFSi(CH_3)_3][B(C_6F_5)_4]$, $B(C_6F_5)_3$, $GaF_3$, $GaCl_3$, $TiF_4$, $TiCl_4$, $PF_5$, $PCl_5$, $Ph_3C[BF_4]$, zeolite or mixtures thereof;

in a even more very preferred embodiment, CAT is $B(C_6F_5)_3$, $GaF_3$, $GaCl_3$, $TiF_4$, $TiCl_4$, $PF_5$, $PCl_5$, $Ph_3C[BF_4]$, zeolite or mixtures thereof.

In another preferred embodiment, CAT is selected from the group consisting of $(CH_3)_3SiFSi(CH_3)_3[B(C_6F_5)_4]$, $[Ph_3C][BF_4]$, $B(C_6F_5)_3$ and mixtures thereof;

more preferably, CAT is $[Ph_3C][BF_4]$.

CATLEWISACID and CAT respectively can be used in immobilized form on a carrier CARR;

CARR is a carrier conventionally used for immobilizing catalysts in heterogeneously catalyzed reactions;

preferably, CARR is selected from the group consisting of epoxide, polystyrene, zeolite, activated carbon and metal oxide;

said metal oxide is preferably selected from the group consisting of $MnO_2$, $Fe_2O_3$, $CO_3O_4$, NiO, CuO, $CuMnO_2$, MgO, $Al_2O_3$, $SiO_2$, $V_2O_5$, $MoO_3$, $WO_3$ and mixed oxides thereof.

Zeolite can be any zeolite, preferably montmorilonte or bentonite, more preferably Montmorillonite K10®, BASF, Germany (also available at Sigma Aldrich, CAS Number 1318-93-0).

Preferably, $Cat^{n+}$ is, more preferably $Cat^{n+}$ and $[(Z^1F_4)^-]$ are, used in the reaction (Rea1) in form of a compound of formula (A1);

$$[Cat^{n+}][(Z^1F_4)^-]_n \qquad (A1)$$

wherein $Cat^{n+}$, $Z^1$ and n are defined herein, also with all their embodiments.

In a preferred embodiment, compound of formula (A1) is reacted with trimethylsilylcyanide in the presence of a catalyst CAT;

with compound of formula (A1) and catalyst CAT as defined herein, also with all their embodiments;

preferably, catalyst CAT is $(CH_3)_3SiFSi(CH_3)_3[B(C_6F_5)_4]$ or $[Ph_3C][BF_4]$, more preferably, catalyst CAT is $[Ph_3C][BF_4]$;

in one preferred embodiment, compound of formula (A1) is different from catalyst CAT;

in another preferred embodiment, compound of formula (A1) is identical with catalyst CAT.

Compound of formula (A1) and catalyst CAT can be one and the same compound, that means compound of formula (A1) can act simultaneously as catalyst CAT and vice versa.

Preferably, CatINORG$^{n+}$ is a cation selected from the 1., 2., 3., 4., 5., 6., 7., 8., 9., 10., 11., 12., 13., 14. or 15. group of the periodic table or is a cation from the lanthanides or is $NH_4^+$;

more preferably, CatINORG$^{n+}$ is a cation selected from the 1., 2., 4., 5., 6., 7., 8., 9., 10., 11., 12., 13., 14. or 15. group of the periodic table or is a cation from the lanthanides or $NH_4^+$;

even more preferably, CatINORG$^{n+}$ is selected from the group consisting of $Li^+$, $Na^+$, $K^+$, $Rb^+$, $Cs^+$, $Be^{2+}$, $Mg^{2+}$, $Ca^{2+}$, $Sr^{2+}$, $Ba^{2+}$, $Ti^{4+}$, $Ti^{3+}$, $Zr^{4+}$, $Zr^{3+}$, $Hf^{4+}$, $Hf^{3+}$, $V^{4+}$, $V^{3+}$, $V^{2+}$, $Nb^{4+}$, $Ta^{4+}$, $Cr^{3+}$, $Mo^{4+}$, $Mo^{3+}$, $Mo^{2+}$, $W^{4+}$, $W^{3+}$, $W^{2+}$, $Mn^{4+}$, $Mn^{3+}$, $Mn^{2+}$, $Fe^{4+}$, $Fe^{3+}$, $Fe^{2+}$, $Ru^{4+}$, $Ru^{3+}$, $Ru^{2+}$, $OS^{4+}$, $OS^{3+}$, $OS^{2+}$, $Co^{4+}$, $Co^{3+}$, $Co^{2+}$, $Rh^{4+}$, $Rh^{3+}$, $Ir^{4+}$, $Ir^{3+}$, $Ni^{4+}$, $Ni^{3+}$, $Ni^{2+}$, $Pd^{4+}$, $Pd^{3+}$, $Pd^{2+}$, $Pt^{4+}$, $Pt^{3+}$, $Pt^{2+}$, $Cu^{4+}$, $Cu^{3+}$, $Cu^{2+}$, $Cu^+$, $Ag^{4+}$, $Ag^{3+}$, $Ag^{2+}$, $Ag^+$, $Au^{3+}$, $Au^{2+}$, $Au^+$, $Zn^{2+}$, $Zn^+$, $Cd^{2+}$, $Cd^+$, $Hg^{2+}$, $Hg^+$, $B^{3+}$, $Al^{3+}$, $Ga^{3+}$, $Ga^+$, $In^{3+}$, $In^{3+}$, $Ti^{3+}$, $Ti^+$, $Ge^{4+}$, $Ge^{2+}$, $Sn^{4+}$, $Sn^{2+}$, $Pb^{4+}$, $Pb^{2+}$, $As^{3+}$, $Sb^{3+}$, $Bi^{3+}$, $Bi^+$, $La^{3+}$, $Nb^{3+}$, $Sm^{3+}$, $Eu^{3+}$, $Gd^{3+}$, and $NH_4^+$;

especially, CatINORG$^{n+}$ is selected from the group consisting of $Li^+$, $Na^+$, $K^+$, $Mg^{2+}$, $Ca^{2+}$, $Ti^{4+}$, $Ti^{3+}$, $Zr^{4+}$, $Zr^{3+}$, $V^{4+}$, $V^{3+}$, $V^{2+}$, $Cr^{3+}$, $Mo^{4+}$, $Mo^{3+}$, $Mo^{2+}$, $W^{4+}$, $W^{3+}$, $W^{2+}$, $Mn^{4+}$, $Mn^{3+}$, $Mn^{2+}$, $Fe^{4+}$, $Fe^{3+}$, $Fe^{2+}$, $Ru^{4+}$, $Ru^{3+}$, $Ru^{2+}$, $Co^{4+}$, $Co^{3+}$, $Co^{2+}$, $Rh^{4+}$, $Rh^{3+}$, $Ir^{4+}$, $Ir^{3+}$, $Ni^{4+}$, $Ni^{3+}$, $Ni^{2+}$, $Pd^{4+}$, $Pd^{3+}$, $Pd^{2+}$, $Pt^{4+}$, $Pt^{3+}$, $Pt^{2+}$, $Cu^{4+}$, $Cu^{3+}$, $Cu^{2+}$, $Cu^+$, $Ag^{4+}$, $Ag^{3+}$, $Ag^{2+}$, $Ag^+$, $Zn^{2+}$, $Zn^+$, $Al^{3+}$, $Ga^{3+}$, $Ga^+$, $In^{3+}$, $In^+$, $Sn^{4+}$, $Sn^{2+}$, $Pb^{4+}$, $Pb^{2+}$, $Sb^{3+}$, $Nb^{3+}$, $Sm^{3+}$, $Eu^{3+}$, $Gd^{3+}$, and $NH_4^+$;

more especially, CatINORG$^{n+}$ is selected from the group consisting of $Li^+$, $Na^+$, $K^+$, $Mg^{2+}$, $Ca^{2+}$, $Ti^{4+}$, $V^{4+}$, $V^{3+}$, $V^{2+}$, $Cr^{3+}$, $Fe^{4+}$, $Fe^{3+}$, $Fe^{2+}$, $Co^{4+}$, $Co^{3+}$, $Co^{2+}$, $Cu^{4+}$, $Cu^{3+}$, $Cu^{2+}$, $Cu^+$, $Ag^{2+}$, $Ag^+$, $Zn^{2+}$, $Zn^+$, $Al^{3+}$, $Sn^{4+}$, $Sn^{2+}$, $Pb^{4+}$, $Pb^{2+}$, $Sb^{3+}$, $Eu^{3+}$, $Gd^{3+}$, and $NH_4^+$;

even more especially, CatINORG$^{n+}$ is selected from the group consisting of $Li^+$, $Na^+$, $K^+$, $Mg^{2+}$, $Ca^{2+}$, $Ti^{4+}$, $V^{4+}$, $V^{3+}$, $Cr^{3+}$, $Fe^{4+}$, $Fe^{3+}$, $Fe^{2+}$, $Co^{4+}$, $Co^{3+}$, $Co^{2+}$, $Cu^{4+}$, $Cu^{3+}$, $Cu^{2+}$, $Cu^+$, $Ag^+$, $Zn^{2+}$, $Al^{3+}$, $Sn^{4+}$, $Sn^{2+}$, $Pb^{4+}$, $Pb^{2+}$, $Gd^{3+}$, and $NH_4^+$;

in particular, CatINORG$^{n+}$ is selected from the group consisting of $Li^+$, $Na^+$, $K^+$, $NH_4^+$, $Ag^+$, $Mg^{2+}$, $Ca^{2+}$, $Zn^{2+}$ and $Cu^{2+}$;

more in particular, CatINORG$^{n+}$ is selected from the group consisting of Li$^+$, Na$^+$, K$^+$, NH$_4^+$, Ag$^+$, Mg$^{2+}$, Ca$^{2+}$ and Zn$^{2+}$;

even more in particular, CatINORG$^{n+}$ is Li$^+$, Na$^+$, K$^+$, Ag$^+$, Mg$^{2+}$, or Zn$^{2+}$;

especially in particular, CatINORG$^{n+}$ is Li$^+$, K$^+$, Ag$^+$, Mg$^{2+}$, or Zn$^{2+}$;

more especially in particular, CatINORG$^{n+}$ is Li$^+$, K$^+$ or Ag$^+$.

Preferably, n in CatInORG$^{n+}$ is 1 or 2.

The term "where applicable" in the definition of CatORG$^{n+}$ means, that any of the optional substituents of the residues R2 to R11 requires a respective site, and e.g. in case of R2 being a perfluorinated side chain no respective site is available any more for a substituent.

Preferably, CatORG$^{n+}$ contains a heteroatom selected from the group consisting of nitrogen, phosphorus, sulfur and oxygen;

more preferably, CatORG$^{n+}$ contains a heteroatom selected from the group consisting of nitrogen and phosphorus.

Preferably,
R16 is selected from the group consisting of C$_{2-6}$ alkylen, C$_{5-6}$ cycloalkylen, phenylen, C(H)(phenyl), R17(—O—R17)$_{n1}$;
R17 is selected from the group consisting of CH$_2$—CH$_2$, CH$_2$—CH$_2$—CH$_2$ and CH$_2$—CH$_2$—CH$_2$—CH$_2$;
R18 and R19 are identical or different and independently from each other selected from the group consisting of H, C$_{1-4}$ alkyl, C$_{5-6}$ cycloalkyl, phenyl and benzyl;
n1 is an integer from 1 to 10;

more preferably,
R16 is selected from the group consisting of C$_{2-4}$ alkylen, C$_6$ cycloalkylen, phenylen, C(H)(phenyl), R17(—O—R17)$_{n1}$;
R17 is selected from the group consisting of CH$_2$—CH$_2$ and CH$_2$—CH$_2$—CH$_2$;
R18 and R19 are identical and selected from the group consisting of H, C$_{1-4}$ alkyl, C$_{5-6}$ cycloalkyl, phenyl and benzyl;
n1 is an integer from 1 to 6;

even more preferably, for n being 2 CatORG$^{n+}$ is (H$_2$(R18)N-R16-N(R19)H$_2$)$^{2+}$;
R16 is selected from the group consisting of C$_{2-4}$ alkylen, phenylen and C(H)(phenyl);
R18 and R19 are identical and selected from the group consisting of H, C$_{1-4}$ alkyl, C$_{5-6}$ cycloalkyl, phenyl and benzyl;

especially, when n is 2, then CatORG$^{n+}$ is (H$_3$N—CH$_2$—CH$_2$—NH$_3$)$^{2+}$.

Preferably, n in CatORG$^{n+}$ is 1.

Preferably, CatORG$^{n+}$ is selected from the group consisting of ammonium, phosphonium, sulfonium, pyrrolidinium, pyrrolinium, pyrrolium, pyrazolium, pyrazolinium, imidazolium, imidazolinium, triazolium, oxazolium, thiazolium, piperidinium, piperazinium, morpholinium, pyridinium, pyridazinium, pyrimidinium, pyrazinium, 1,3-dioxolium, pyrylium, thiopyrylium, quinoxalinium, indolinium, indolium, [(CH$_3$)$_3$SiFSi(CH$_3$)$_3$]$^+$, Ph$_3$C$^+$, and mixtures thereof;

more preferably from the group consisting of ammonium, phosphonium, sulfonium, pyrrolidinium, pyrrolinium, pyrrolium, pyrazolium, imidazolium, triazolium, oxazolium, thiazolium, piperidinium, piperazinium, morpholinium, pyridinium, pyridazinium, pyrimidinium, pyrazinium, 1,3-dioxolium, pyrylium, thiopyrylium, [(CH$_3$)$_3$SiFSi(CH$_3$)$_3$]$^+$, Ph$_3$C$^+$, and mixtures thereof.

More preferably, CatORG$^{n+}$ is selected from the group consisting of

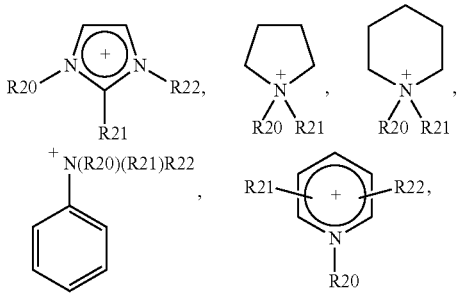

[N(R20)(R21)(R22)R23]$^+$, [P(R20)(R21)(R22)R23]$^+$, [(CH$_3$)$_3$SiFSi(CH$_3$)$_3$]$^+$, Ph$_3$C$^+$, and mixtures thereof;

wherein
R20, R21, R23 are identical or different and independently from each other selected from the group consisting of H, C$_{1-20}$ alkyl, C$_{3-10}$ cycloalkyl and allyl;
R22 is C$_{1-20}$ alkyl, C$_{3-10}$ cycloalkyl or allyl;

preferably,
R20, R21, R23 are identical or different and independently from each other selected from the group consisting of H, C$_{1-14}$ alkyl, C$_{5-8}$ cycloalkyl and allyl;
R22 is C$_{1-14}$ alkyl, C$_{5-8}$ cycloalkyl or allyl;

more preferably,
R20, R21, R23 are identical or different and independently from each other selected from the group consisting of H, C$_{1-8}$ alkyl, C$_{5-7}$ cycloalkyl and allyl;
R22 is C$_{1-8}$ alkyl, C$_{5-7}$ cycloalkyl or allyl;

even more preferably, CatORG$^{n+}$ is selected from the group consisting of

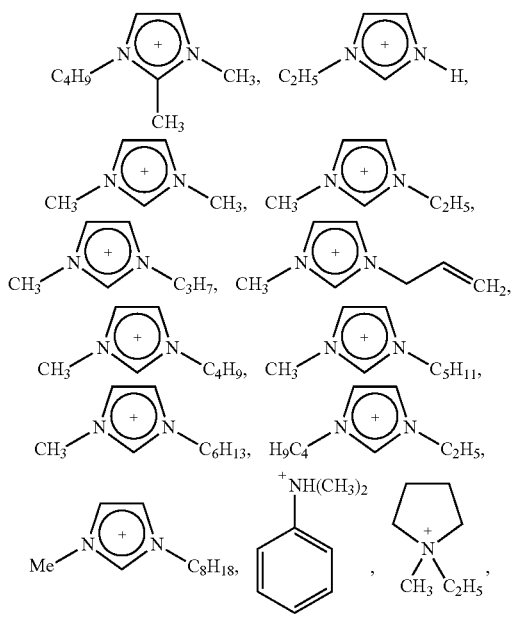

-continued

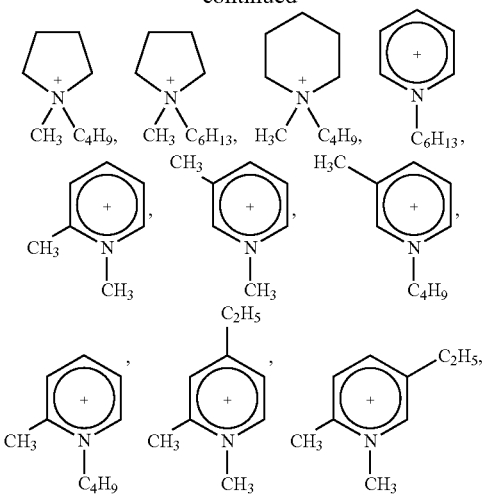

[NH(C$_2$H$_5$)$_3$]$^+$, [NH(C$_3$H$_7$)$_3$]$^+$, [NH(C$_4$H$_9$)$_3$]$^+$, [N(C$_2$H$_5$)$_4$]$^+$, [N(C$_3$H$_7$)$_4$]$^+$, [N(C$_4$H$_9$)$_4$]$^+$, [P(C$_2$H$_5$)$_4$]$^+$, [P(C$_3$H$_7$)$_4$]$^+$, [P(C$_4$H$_9$)$_4$]$^+$, [P(C$_6$H$_{13}$)$_3$(C$_{14}$H$_{29}$)]$^+$, [(CH$_3$)$_3$SiFSi(CH$_3$)$_3$]$^+$, Ph$_3$C$^+$, and mixtures thereof;

especially, CatORG$^{n+}$ is selected from the group consisting of

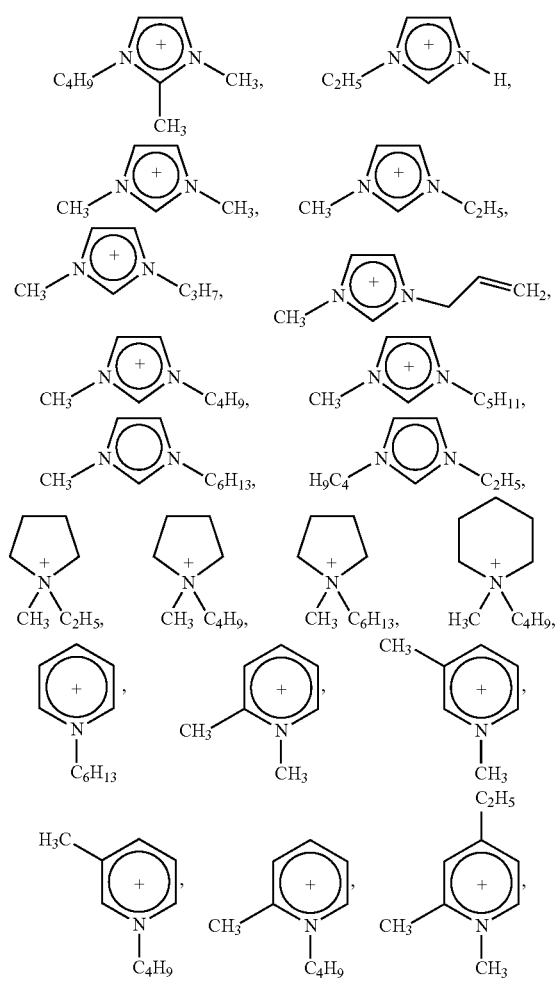

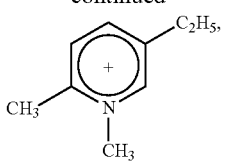

[NH(C$_2$H$_5$)$_3$]$^+$, [NH(C$_4$H$_9$)$_3$]$^+$, [N(C$_2$H$_5$)$_4$]$^+$, [NH(C3H7)4]$^+$, [N(C$_4$H$_9$)$_4$]$^+$, [P(C$_2$H$_5$)$_4$]$^+$, [P(C$_3$H$_7$)$_4$]$^+$, [P(C$_4$H$_9$)$_4$]$^+$, [(CH$_3$)$_3$SiFSi(CH$_3$)$_3$]$^+$, Ph$_3$C$^+$, and mixtures thereof.

more especially, CatORG$^{n+}$ is selected from the group consisting of

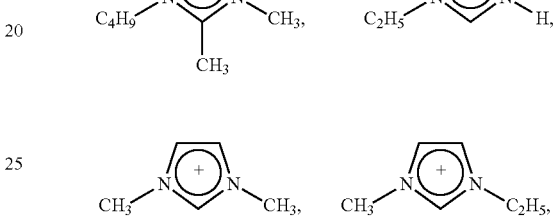

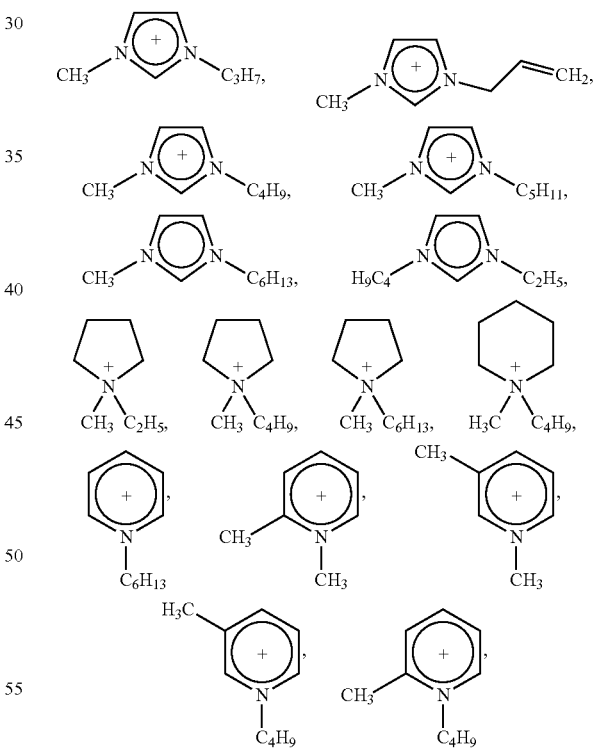

[NH(C$_2$H$_5$)$_3$]$^+$, [NH(C$_4$H$_9$)$_3$]$^+$, [N(C$_2$H$_5$)$_4$]$^+$, [N(C$_3$H$_7$)$_4$]$^+$, [N(C$_4$H$_9$)$_4$]$^+$, [P(C$_2$H$_5$)$_4$]$^+$, [P(C$_3$H$_7$)$_4$]$^+$, [P(C$_4$H$_9$)$_4$]$^+$, [(CH$_3$)$_3$SiFSi(CH$_3$)$_3$]$^+$, Ph$_3$C$^+$, and mixtures thereof.

In particular, Cat$^{n+}$ is a cation (Cat-Part1);

cation (Cat-Part1) is CatINORG$^{n+}$ or CatORG$^{n+}$, with CatINORG selected from the group consisting of Li$^+$, Na$^+$, K$^+$, NH$_4^+$, Ag$^+$, Mg$^{2+}$, Ca$^{2+}$ and Zn$^{2+}$;

and
with CatORG$^{n+}$ selected from the group consisting of

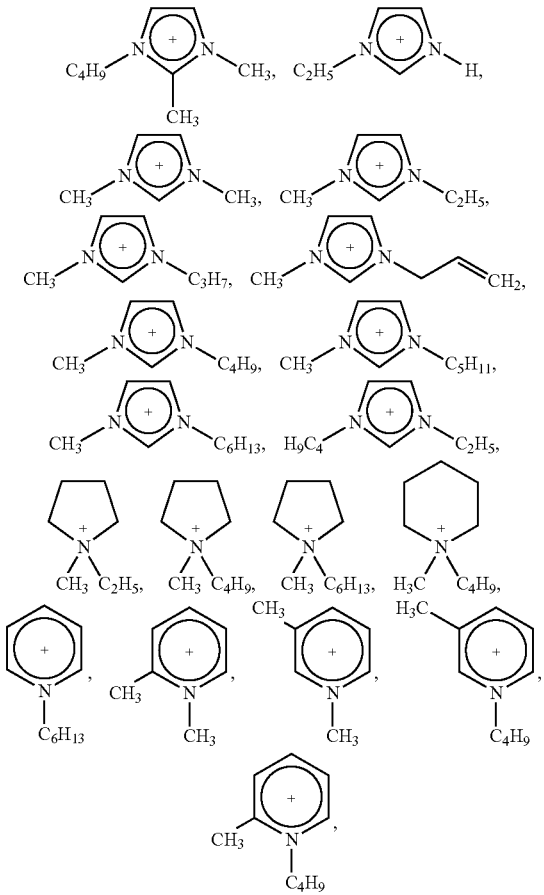

[NH(C$_2$H$_5$)$_3$]$^+$, [NH(C$_4$H$_9$)$_3$]$^+$, [N(C$_2$H$_5$)$_4$]$^+$, [N(C$_3$H$_7$)$_4$]$^+$, [N(C$_4$H$_9$)$_4$]$^+$, [P(C$_2$H$_5$)$_4$]$^+$, [P(C$_3$H$_7$)$_4$]$^+$, [P(C$_4$H$_9$)$_4$]$^+$, [(CH$_3$)$_3$SiFSi(CH$_3$)$_3$]$^+$, Ph$_3$C$^+$, and mixtures thereof.

Even more preferably, compound of formula (I) is compound (Group-I), compound (Group-I) is selected from the group consisting of compound of formula (Ia) and compound of formula (Ib);

Cat$^{n+}$ and n are as defined above, also with all their embodiments, preferably Cat$^{n+}$ is cation (Cat-Part1).

A special embodiment of compound of formula (I) is compound (GROUP-II), compound (GROUP-II) is selected from the group consisting of K$^+$[(BF(CN)$_3$)$^-$], Ag$^+$[(BF(CN)$_3$)$^-$], Li$^+$[(BF(CN)$_3$)$^-$], Mg$^{2+}$[(BF(CN3)$^-$]$_2$, Ca$^{2+}$[(BF(CN)$_3$)$^-$]$_2$, [N(n-Pr)$_4$]$^+$[(BF(CN)$_3$)$^-$], [N(n-Bu)$_4$]$^+$[(BF(CN)$_3$)$^-$], [P(n-Bu)$_4$]$^+$[(BF(CN)$_3$)$^-$], 1,3-dimethylimidazolium [(BF(CN)$_3$)$^-$], 1-ethyl-3-methylimidazolium [(BF(CN)$_3$)$^-$], 1-propyl-3-methylimidazolium [(BF(CN)$_3$)$^-$] and mixtures thereof.

Another special embodiment of compound of formula (I) is compound (GROUP-III), compound (GROUP-III) is selected from the group consisting of K$^+$[((B(CN)$_4$)$^-$], Ag$^+$[((B(CN)$_4$)$^-$], Li$^+$[((B(CN)$_4$)$^-$], Mg$^{2+}$[(B(CN)$_4$)$^-$]$_2$, Ca$^{2+}$[(B(CN)$_4$)$^-$]$_2$, [N(n-Pr)$_4$]$^+$[(B(CN)$_4$)$^-$], [N(n-Bu)$_4$]$^+$ [(B(CN)$_4$)$^-$], [P(n-Bu)$_4$]$^+$[(B(CN)$_4$)$^-$], 1,3-dimethylimidazolium [(B(CN)$_4$)$^-$], 1-ethyl-3-methylimidazolium [(B(CN)$_4$)$^-$], 1-propyl-3-methylimidazolium [(B(CN)$_4$)$^-$] and mixtures thereof.

Yet another special embodiment of compound of formula (I) is compound (GROUP-IV), compound (GROUP-IV) is selected from the group consisting of K$^+$[((B(F)$_2$(CN)$_2$)$^-$], Ag$^+$[((B(F)$_2$(CN)$_2$)$^-$], Li$^+$[(B(F)$_2$(CN)$_2$)$^-$], Mg$^{2+}$[(B(F)$_2$(CN)$_2$)$^-$]$_2$, Ca$^{2+}$[(B(F)$_2$(CN)$_2$)$^-$]$_2$, [N(n-Pr)$_4$]$^+$[(B(F)$_2$(CN)$_2$)$^-$], [N(n-Bu)$_4$]$^+$[(B(F)$_2$(CN)$_2$)$^-$], [P(n-Bu)$_4$]$^+$[(B(F)$_2$(CN)$_2$)$^-$], 1,3-dimethylimidazolium [(B(F)$_2$(CN)$_2$)$^-$], 1-ethyl-3-methylimidazolium [(B(F)$_2$(CN)$_2$)$^+$], 1-propyl-3-methylimidazolium [(B(F)$_2$(CN)$_2$)$^-$] and mixtures thereof.

Another special embodiment of compound of formula (I) is compound (GROUP-V), compound (GROUP-V) is selected from the group consisting of K$^+$[((B(F)$_3$(CN))$^-$], Ag$^+$[((B(F)$_3$(CN))$^-$], Li$^+$[((B(F)$_3$(CN))$^-$], Mg$^{2+}$[(B(F)$_3$(CN))$^-$]$_2$, Ca$^{2+}$[(B(F)$_3$(CN))$^-$]$_2$, [N(n-Pr)$_4$]$^+$[(B(F)$_3$(CN))$^-$], [N(n-Bu)$_4$]$^+$[(B(F)$_3$(CN))$^-$], [P(n-Bu)$_4$]$^+$[(B(F)$_3$(CN))$^-$], 1,3-dimethylimidazolium [(B(F)$_3$(CN))$^-$], 1-ethyl-3-methylimidazolium [(B(F)$_3$(CN))$^-$], 1-propyl-3-methylimidazolium [(B(F)$_3$(CN))$^-$] and mixtures thereof.

In particular, compound of formula (I) is compound (GROUP), compound (GROUP) is selected from the group consisting of compound of formula (1), compound of formula (2), compound of formula (3), compound of formula (4), compound of formula (5), compound of formula (6), compound of formula (7), compound of formula (8), compound of formula (9), compound of formula (10), and mixtures thereof.

| | |
|---|---|
| [(n-Bu)$_4$N][BF(CN)$_3$] | (1) |
| [EMIm][BF(CN)$_3$] | (2) |
| [(n-Bu)$_4$N][BF$_3$(CN)] | (3) |
| [(n-Bu)$_4$N][BF$_2$(CN)$_2$] | (4) |
| [(n-Bu)$_4$N][B(CN)$_4$] | (5) |
| K[BF(CN)$_3$] | (6) |
| K[B(CN)$_4$] | (7) |
| [BMIm][B(CN)$_4$] | (8) |
| Li[BF(CN)$_3$] | (9) |
| Li[B(CN)$_4$] | (10) |

Preferably, from 1 to 40 mol equivalents, more preferably 4 to 35 mol equivalents, even more preferably from 6 to 25 mol equivalents, especially from 6 to 15 mol equivalents, of trimethylsilylcyanide are used in reaction (Rea1), the mol equivalents being based on the molar amount of the anion [(Z$^1$F$_4$)$^-$].

Preferably, when CATLEWISACID is an uncharged compound, then the molar amount of Cat$^{n+}$ is equal to the molar amount of anion [(Z$^1$F$_4$)$^-$].

Preferably, when CATLEWISACID is a cation, then the combined molar amount of CATLEWISACID and Cat$^{n+}$ is 1-fold to 40-fold, more preferably 1-fold to 35-fold, even more preferably 1-fold to 25-foled, especially 1-fold to 15-fold, more especially 1-fold to 10-fold, even more especially 1-fold to 5-fold, in particular 1-fold to 2-fold, of the molar amount of the anion [(Z$^1$F$_4$)$^-$].

Preferably, from 0.0001 to 40 mol equivalents, more preferably 0.001 to 35 mol equivalents, even more preferably from 0.005 to 25 mol equivalents, especially from 0.005 to 25 mol equivalents, more especially from 0.005 to 15 mol equivalents, even more especially from 0.005 to 5 mol equivalents, of CATLEWISACID are used in reaction (Rea1), the mol equivalents being based on the molar amount of the anion $[(Z^1F_4)^-]$.

In another preferable embodiment, from 0.01 to 40 mol %, more preferably 0.1 to 35 mol %, even more preferably 0.1 to 25 mol %, especially from 0.5 to 15 mol %, more especially from 0.5 to 10 mol %, even more especially from 0.5 to 5 mol %, of CATLEWISACID are used in reaction (Rea1), the mol % being based on the molar amount of the anion $[(Z^1F_4)^-]$.

When reaction (Rea1) is done by reacting compound of formula (A1) with trimethylsilylcyanide in the presence of a catalyst CAT, and when compound of formula (A1) is different from catalyst CAT, then preferably, from 1 to 40 mol equivalents, more preferably 4 to 35 mol equivalents, even more preferably from 5 to 25 mol equivalents, especially from 5 to 15 mol equivalents, more especially from 5 to 10 mol equivalents, of trimethylsilylcyanide are used in reaction (Rea1), the mol equivalents being based on the molar amount of compound of formula (A1); and preferably, from 0.01 to 40 mol %, more preferably 0.1 to 35 mol %, even more preferably 0.1 to 25 mol %, especially from 0.5 to 15 mol %, more especially from 0.5 to 10 mol %, even more especially from 0.5 to 5 mol %, of catalyst CAT are used in reaction (Rea1), the mol % being based on the combined molar amount of compound of formula (A1) and catalyst CAT;

whereas when compound of formula (A1) is identical with catalyst CAT, then preferably, from 1 to 40 mol equivalents, more preferably 4 to 35 mol equivalents, even more preferably from 5 to 25 mol equivalents, especially from 5 to 15 mol equivalents, more especially from 5 to 10 mol equivalents, of trimethylsilylcyanide are used in reaction (Rea1), the mol equivalents being based on the combined molar amount of compound of formula (A1) and catalyst CAT.

The reaction temperatures of reaction (Rea1) is preferably from −75 to 150° C., more preferably from −50 to 120° C., more preferably from −50 to 100° C., even more preferably −50 to 80° C.

Another possible range of the reaction temperatures of reaction (Rea1) is preferably from −10 to 150° C., more preferably from −10 to 120° C., more preferably from 0 to 100° C., even more preferably 10 to 80° C.

Reaction (Rea1) can be done in a closed system and at the pressure caused by the chosen temperature.

The reaction time of reaction (Rea1) is preferably from 15 min to 96 h, more preferably from 20 min to 85 h, even more preferably from 20 min to 48 h.

Another possible range of the reaction time of reaction (Rea1) is preferably from 30 min to 96 h, more preferably from 1 h to 85 h, even more preferably from 1 h to 48 h.

Preferably, reaction (Rea1) is done under inert atmosphere. Preferably, the inert atmosphere is achieved by the use if an inert gas preferably selected from the group consisting of argon, another noble gas, lower boiling alkane, nitrogen and mixtures thereof.

The lower boiling alkane is preferably a $C_{1-3}$ alkane, i.e. methane, ethane or propane.

After the reaction, compound of formula (I) can be isolated by standard methods such as evaporation of volatile components, extraction, washing, drying, concentration, crystallization, chromatography and any combination thereof, which are known per se to the person skilled in the art.

Preferably, after the reaction the reaction product is treated with hydrogen peroxide, preferably with aqueous hydrogen peroxide.

More preferably for isolation, the reaction product is mixed with aqueous hydrogen peroxide to provide a mixture (M).

Preferably, the concentration of the aqueous hydrogen peroxide is from 10 to 40 wt % hydrogen peroxide, the wt % based on the total weight of the aqueous hydrogen peroxide.

Preferably, from 1 to 30 mol equivalents, more preferably from 1 to 20 mol equivalents, of hydrogen peroxide are used, the mol equivalents being based on the molar amount of compound of formula (A1).

Preferably mixture (M) is stirred for 5 min to 12 h, more preferably for 10 min to 6 h.

Preferably mixture (M) is stirred at a temperature (M), temperature (M) is preferably from ambient temperature to 100° C.

After treatment with hydrogen peroxide, mixture (M) is preferably filtrated. The residue of the filtration is preferably washed with a solvent (WASH), solvent (WASH) is preferably water or an ether such as diethylether, more preferably diethylether.

Preferably, the method comprises additionally to step (St1) a step (St2), step (St2) is done after step (St1); step (St2) comprises a reaction (Rea2), reaction (Rea2) is a metathesis reaction wherein cation $Cat^{n+}$ in compound of formula (I) is exchanged for a cation different from $Cat^{n+}$; compound of formula (I) having been prepared in step (St1); $Cat^{n+}$, n, compound of formula (I) and step (St1) are as defined above, also with all their embodiments.

Preferably, reaction (Rea2) provides for the preparation of a compound of formula (I-Cat-r);

$[Cat\text{-}r^{r+}][(Z^1F_{4-m}(CN)_m)^-]_r$     (I-Cat-r)

$Cat\text{-}r^{r+}$ is selected from the group consisting of CatINORG$^{n+}$ and CatORG$^{n+}$ and is different from $Cat^{n+}$;

r is 1, 2, 3 or 4;

with step (St1), $Z^1$, m, CatINORG$^{n+}$ and CatORG$^{n+}$ as defined above, also with all their embodiments.

Preferably, in reaction (Rea2) $Cat^{n+}$ is exchanged for $Cat\text{-}r^{r+}$ from a compound of formula (I-Cat-n);

$(Cat\text{-}r^{r+})_{t1}(AnINORG^{q-})_{t2}$     (I-Cat-n)

q is 1 or 2;

t1 is 1 or 2;

t2 is 1, 2, 3 or 4;

when r is 1 and q is 1, then t1 is 1 and t2 is 1;
when r is 2 and q is 1, then t1 is 1 and t2 is 2;
when r is 3 and q is 1, then t1 is 1 and t2 is 3;
when r is 4 and q is 1, then t1 is 1 and t2 is 4;
when r is 1 and q is 2, then t1 is 2 and t2 is 1;
when r is 2 and q is 2, then t1 is 1 and t2 is 1;
when r is 3 and q is 2, then t1 is 2 and t2 is 3;
when r is 4 and q is 2, then t1 is 1 and t2 is 2;

AnINORG$^{q-}$ is an anion selected from the group consisting of halide, OH$^-$, CN$^-$, OCN$^-$, SCN$^-$, N$_3^-$, sulfate, hydrogensulfate, nitrate, CO$_3^{2-}$, HCO$_3^-$, BF$_4^-$, PF$_6^-$, $SbF_6^-$, $CF_3SO_3^-$, $(CF_3SO_2)_2N^-$, $(FSO_2)_2N^-$, $C_{1-6}$ alkyl-$SO_3^-$, $C_{1-6}$ alkyl-O-$SO_3^-$,

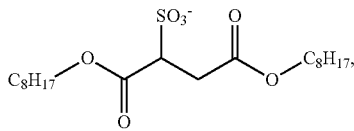

anions of $C_{1-20}$ monocarboxylic aliphatic acids, mono- and dianions of $C_{2-6}$ dicarboxylic aliphatic acids, anions of benzoic acids, mono- and dianions of phthalic acids, of isophthalic acids and of terephthalic acids, $N(CN)_2^-$, $C(CN)_3^-$, $B(CN)_4^-$, $P(CN)_6^-$, $Sb(CN)_6^-$, and mixtures thereof;

Cat-$r'^+$, r, CatINORG$^{n+}$ and CatORG$^{n+}$ are as defined above, also with all their embodiments.

Reaction (Rea2) is a metathesis reaction, also called a salt-exchange reaction. In a metathesis reaction such as reaction (Rea2) a first cation in a first salt is exchanged for a second cation, said second cation coming from a second salt.

Preferably, AnINORG$^{q-}$ is an anion selected from the group consisting of halide, $OH^-$, $CN^-$, sulfate, hydrogensulfate, nitrate, $CO_3^{2-}$, $HCO_3^-$, $BF_4^-$, $PF_6^-$, $CF_3SO_3^-$, $(CF_3SO_2)_2N^-$, $(FSO_2)_2N^-$, $H_3C-SO_3^-$, $H_3C-CH_2-SO_3^-$, $H_3C-O-SO_3^-$, $H_3C-CH_2-O-SO_3^-$, acetate, oleate, fumarate, maleate, oxalate, benzoate, $N(CN)_2^-$, and mixtures thereof;

more preferably, AnINORG$^{q-}$ is an anion selected from the group consisting of $Br^-$, $Cl^-$, $OH^-$, $CN^-$, sulfate, hydrogensulfate, $CO_3^{2-}$, $HCO_3^-$, acetate, and mixtures thereof;

even more preferably, AnINORG$^{q-}$ is an anion selected from the group consisting of $Cl^-$, $OH^-$, $CN^-$, sulfate, hydrogensulfate, $CO_3^{2-}$, $HCO_3^-$, acetate, and mixtures thereof.

In another preferred embodiment, AnINORG$^{q-}$ is an anion selected from the group consisting of halide, $OH^-$, $CN^-$, $OCN^-$, $SCN^-$, $N_3^-$, sulfate, hydrogensulfate, nitrate, $CO_3^{2-}$, $HCO_3^-$, $BF_4^-$, $PF_6^-$, $SbF_6^-$, $CF_3SO_3^-$, $(CF_3SO_2)_2N^-$, $(FSO_2)_2N^-$, $C_{1-6}$ alkyl-$SO_3^-$, $C_{1-6}$ alkyl-O-$SO_3^-$,

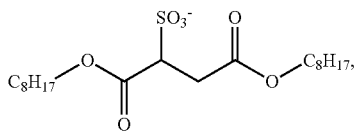

anions of $C_{1-20}$ monocarboxylic aliphatic acids, anions of $C_{2-6}$ dicarboxylic aliphatic acids, benzoate, phthalates, $N(CN)_2^-$, $C(CN)_3^-$, $B(CN)_4^-$, $P(CN)_6^-$, $Sb(CN)_6^-$, and mixtures thereof.

Preferably, r is 1 or 2.

In case of reaction (Rea2), preferably a compound of formula (I-Cat-r) with Cat-$r'^+$ being CatORG$^{n+}$ is prepared by exchange of a Cat$^{n+}$ being a CatINORG$^{n+}$ in compound of formula (I) for a CatORG$^{n+}$.

Said CatORG$^{n+}$ is provided in reaction (Rea2) preferably in form of a compound of formula (I-CatORG)

$(CatORG^{n+})_q(AnINORG^{q-})_n$ (I-CatORG)

wherein

Cat$^{n+}$, n, CatORG$^{n+}$, CatINORG$^{n+}$, q and AnINORG$^{q-}$ are as defined above, also with all their embodiments.

Preferably, in reaction (Rea2) the cation different from Cat$^{n+}$, that is preferably Cat-$r'^+$, is present in at least such a molar amount relative to the molar amount of Cat$^{n+}$ as required for a stoichiometric exchange of said two cations;

more preferably, compound of formula (I) and compound of formula (I-Cat-n) are present in at least such a molar amount relative to each other, that Cat$^{n+}$ is stoichiometrically exchanged for Cat-$r'^+$.

Even more preferably, the molar amount of compound of formula (I-Cat-n) is such, that from 1 to 1.5, even more preferably from 1 to 1.2, required equivalents of Cat-$r'^+$ relative to the equivalents of Cat$^{n+}$ are present.

The reaction temperatures of reaction (Rea2) is preferably from 0 to 250° C., more preferably from 10 to 200° C., even more preferably from 10 to 150° C., especially from 10 to 100° C., more especially from 10 to 50° C.

The reaction (Rea2) is preferably carried out in a solvent (Sol2), solvent (Sol2) is preferably selected from the group consisting of water, DCM, ethyl acetate, $C_{5-10}$ alkane, and mixtures thereof.

$C_{5-10}$ alkane is preferably pentane, hexane or heptane.

In a more preferred embodiment, reaction (Rea2) is done in DCM or in a biphasic solvent system of water and DCM.

As an alternative, the reaction can also be carried out in the absence of a solvent or in a solvent in which the inorganic salt formed as side product is sparingly soluble or insoluble. As a further alternative, it is also possible to carry out the reaction in an aqueous solution using an ion exchanger loaded with the desired cation Cat$^{n+}$.

The amount of solvent is preferably from 2 to 40 fold, more preferably from 3 to 20 fold, of the weight of compound of formula (I).

Reaction (Rea2) can be done in a closed system and at the pressure caused by the chosen temperature.

The reaction time of reaction (Rea2) is preferably from 15 min to 96 h, more preferably from 15 min to 48 h, even more preferably from 15 min to 24 h.

Preferably, reaction (Rea2) is done under inert atmosphere. Preferably, the inert atmosphere is achieved by the use if an inert gas preferably selected from the group consisting of argon, another noble gas, lower boiling alkane, nitrogen and mixtures thereof.

The lower boiling alkane is preferably a $C_{1-3}$ alkane, i.e. methane, ethane or propane.

Subsequent to reaction (Rea2) there can be a further metathesis reaction or further metathesis reactions.

After reaction (Rea2), compound of formula (I) can be isolated from the reaction mixture by standard methods such as filtration, evaporation of volatile components, extraction, washing, drying, concentration, crystallization, chromatography and any combination thereof, which are known per se to the person skilled in the art.

For example, when reaction (Rea2) was done in a biphasic solvent system of water and DCM, the aqueous and organic phases are separated, the organic phase is preferably washed, preferably with water, then preferably dried, preferably with $Na_2SO_4$, $K_2CO_3$, $CaCl_2$ or $MgSO_4$, and finally evaporated.

Or as another example, when reaction (Rea2) was done in DCM and a suspension was formed, filtration and evaporation of the solvent will isolate the product.

It is possible use compound of formula (I), which was obtained by the method of instant invention, as substrate in a similar reaction with trimethylsilylcyanide.

Therefore the method of instant invention can comprise additionally to step (St1) a step (St1-1), step (St1-1) is done after step (St1);

step (St1-1) comprises a reaction (Rea1-1), wherein compound of formula (I), obtained in step (1), is reacted with trimethylsilylcyanide;

preferably the reaction (Rea(1-1) is done in the presence of CATLEWISACID;

with CATLEWISACID as defined above, also in all its embodiments.

Compounds of formula (A1) are commercially available depending on the cation $Cat^{n+}$, e.g. $[(n-Bu_4)N][BF_4]$ and $K[BF_4]$ are commercially available, as well as catalyst CAT. Other compounds of formula (A1) with cations $Cat^{n+}$ different from $K^+$ and $(n-Bu_4)N^+$, and which are not commercially available, can be prepared by conventional metathesis reaction, i.e. substitution of the respective cation $K^+$ or $(n-Bu_4)N^+$ against another cation.

EXAMPLES

Methods $^1H$, $^{13}C$, $^{19}F$ and $^{31}P$ NMR spectra were recorded on a Bruker AVANCE 300 and Bruker AVANCE 250 instruments in $CD_3CN$, $CDCl_3$, $D_6$-DMSO, $D_2O$ or $CD_2Cl_2$. Chemical shifts are expressed in parts per million referred to TMS in case of $^1H$ and $^{13}C$, $C^{19}FCl_3$ in case of $^{19}F$, and $H_3^{31}PO_4$ in case of $^{31}P$, and coupling constants (J) in Hertz. When a % value for the amount of compounds is stated based on NMR measurement, the % value represents an area-%, the area-% being based on the total area of peaks in the spectrum. In case of the individual amount of a component in a mixtures the stated % value for the amount of the component in the mixture represents an area-%, this area-% being based on the combined area of peaks of all components of the mixture; if not stated otherwise.

IR-spectra were recorded on a Nicolet 380 FT-IR spectrometer. Measurements were done at room temperature.

RAMAN-spectra were recorded on a LabRAM HR 800 Horiba Jobin YVON. Measurements were done at room temperature.

The C/H/N-analyses were measured on a C/H/N/S-Analysator (Thermoquest Flash EA 1112).

Melting points and temperature of decomposition $T_{dec}$ were measured on a DSC 823e from Mettler-Toledo. The calibration was carried out with the melting points of In (156.6±0.3° C.) and Zn (419.6±0.7° C.) with an heating rate of 5 K per min.

Preparation Description A: Synthesis of $[(n-Bu)_4N][BF_4]$

A solution of $[(n-Bu_4)N]Br$ (8.05 g, 24.98 mmol) in 50 ml of $CH_2Cl_2$ was added to the solution of $K[BF_4]$ (3.12 g, 24.78 mmol) in 30 ml of $H_2O$. After stirring for 24 h at ambient temperature the phases were separated. The organic phase was washed three times with 10 ml of water, dried over anhydrous $Mg_2SO_4$ and filtered. The filtrate was concentrated on a rotary evaporator to obtain a white solid. The obtained solid was dried at 90° C. in vacuo for 15 hours. The yield of $[(n-Bu_4)N][BF_4]$ was 7.83 g (96%, 23.8 mmol).

DSC (10 $Kmin^{-1}$): m.p.=153° C.

C/H/N Analysis calc. % (found): C 58.36 (58.48), H 11.02 (10.84), N 4.25 (4.13)

$^1H$ NMR (25° C., $CD_3CN$, 300.13 MHz, delta in ppm): 0.96 (t, 12H, $CH_3$), 1.35 (m, 8H, $CH_3$—$CH_2$, 1.61 (m, 8H, $CH_2$—$CH_2N$), 3.11 (m, 8H, $NCH_2$)

$^{13}C$ NMR (25° C., $CD_3CN$, 250.13 MHz, delta in ppm): 14.42 (s, 4C, $CH_3$), 20.94 (m, 4C, $CH_3$—$CH_2$), 24.95 (m, 4C, $CH_2$—$CH_2N$), 59.93 (m, 4C, $NCH_2$)

$^{11}B$ NMR (25° C., $CD_3CN$, 96.29 MHz, delta in ppm): −1.18 (s, 1B, $BF_4$)

$^{19}F$ NMR (25° C., $CD_3CN$, 300.13 MHz, delta in ppm): −151.61 (s, 4F, $BF_4$)

IR (ATR, 32 scans, v in $cm^{-1}$): 2960 (m), 2935 (w), 2875 (w), 1486 (m), 1468 (w), 1382 (w), 1285 (w), 1152 (w), 1093 (m), 1047 (s), 1034 (s), 881 (w), 800 (w), 739 (w)

RAMAN (460 mW, 150 scans, v in $cm^{-1}$): 2964 (7), 2933 (10), 2876 (10), 2746 (1), 1453 (4), 1327(2), 1153(1), 1137 (2), 911 (2), 880 (1), 766 (1), 256 (2), 79 (1)

Preparation Description B: Synthesis of $EMIm[BF_4]$ $K[BF_4]$ (0.43 g, 3.4 mmol) and 1-ethyl-3-methylimidazolium bromide (0.50 g, 3.4 mmol) were suspended in 50 ml of acetone. After stirring for 24 hours under argon atmosphere at ambient temperature the suspension was filtered. The solvent was removed in vacuo to obtain a light yellow oil. The product was dried at 90° C. in vacuo for 5 hours to yield 0.61 g (91%, 3.1 mmol) of $EMIm[BF_4]$.

DSC (10 $Kmin^{-1}$): m.p.=16° C.

C/H/N Analysis calc. % (found): C 36.40 (36.32), H 5.60 (5.58), N 14.15 (12.90)

$^1H$ NMR (25° C., $CD_3CN$, 300.13 MHz, delta in ppm): 1.42 (t, 3H, $CH_3$), 3.82 (s, 3H, $NCH_3$), 4.16 (q, 2H, $CH_2$), 7.37 (m, 1H, EtNCH), 7.43 (m, 1H, MeNCH), 8.57 (s, 1H, NCHN)

$^{13}C$ NMR (25° C., $CD_3CN$, 300.13 MHz, delta in ppm): 15.53 (s, 1C, $NCH_2$—$CH_3$), 36.73 (s, 1C, $NCH_3$), 45.80 (s, 1C, $NCH_2$), 123.01 (s, 1C, EtNCH), 124.64 (s, 1C, MeNCH), 136.98 (s, 1C, NCHN)

$^{11}B$ NMR (25° C., $CD_3CN$, 96.29 MHz, delta in ppm): −1.11 (s, 1B, $BF_4$)

$^{19}F$ NMR (25° C., $CD_3CN$, 300.13 MHz, delta in ppm): −151.23 (s, 4F, $BF_4$)

IR (ATR, 32 scans, v in $cm^{-1}$): 3163 (w), 3122 (w), 2989 (w), 2949 (w), 1574 (m), 1455 (w), 1432 (w), 1392 (w), 1336 (w), 1286 (w), 1170 (m), 1015 (s), 845 (m), 805 (w), 753 (m), 701 (w), 648 (m), 622 (m), 598 (w)

Example 1

$[Ph_3C][BF_4]$ (207 mg, 0.63 mmol) and $(CH_3)_3SiCN$ (625 mg, 6.3 mmol) were stirred at ambient temperatures under argon atmosphere. After two hours of stirring an $^{11}B$ NMR was measured. In accordance to $^{11}B$ NMR the product contained only $[BF(CN)_3]^-$. After 20 hours of stirring another $^{11}B$ NMR was measured. In accordance to $^{11}B$ NMR the product contained only $[B(CN)_4]^-$.

Example 2

$[EMIm][BF_4]$ (771 mg, 3.89 mmol), prepared according to Preparation Description B, $[Ph_3C][BF_4]$ (0.01 g, 0.8 mol %, the mol % being based on the combined molar amount of $[EMIm][BF_4]$ and $[Ph_3C][BF_4]$) and $(CH_3)_3SiCN$ (3.87 g, 39 mmol) were stirred under argon atmosphere at ambient temperatures for Tx h. Then a $^{11}$B NMR of the reaction mixture was measured and [Ph$_3$C][BF$_4$] was added, in order to have a desired mol% of [Ph$_3$C][BF$_4$]. Table 2 shows the details, Tx and the percentage of [BF$_3$(CN)]$^-$ [BF$_2$(CN)$_2$]$^-$ and [BF(CN)$_3$]$^-$ in the reaction mixture according to the NMR spectra.

TABLE 2

| Tx [h] | [Ph$_3$C][BF$_4$] Desired [mol %] | [Ph$_3$C][BF$_4$] Added [mg] | [BF$_3$(CN)]$^-$ [%] | [BF$_2$(CN)$_2$]$^-$ [%] | [BF(CN)$_3$]$^-$ [%] |
|---|---|---|---|---|---|
| 0 | 0.8 | 0.01 | — | — | — |
| 70 | 1.5 | 0.02 | 91 | 9 | — |
| 87 | 3 | 0.04 | — | 93 | 7 |
| 103 | — | — | — | — | 100 |

Final $^{11}$B NMR of EMIm[BF(CN)$_3$] (25° C., CD$_3$CN, 96.29 MHz, delta in ppm): −3.70 (q, 1B, BF$_3$(CN)), −7.61 (t, 1B, BF$_2$(CN)$_2$), −17.88 (d, 1B, BF(CN)$_3$)

Example 3

[(n-Bu)$_4$N][BF$_4$] (1.189 g, 3.6 mmol), prepared according to Preparation Description A, [Ph$_3$C][BF$_4$] (3.6 mol %, the mol % being based on the combined molar amount of [(n-Bu)$_4$N][BF$_4$] and [Ph$_3$C][BF$_4$], 44 mg) and (CH$_3$)$_3$SiCN (3.55 g, 36 mmol) were stirred under argon atmosphere at ambient temperatures for 19 h. The excess (CH$_3$)$_3$SiCN and any (CH$_3$)$_3$SiF were removed in vacuo resulting in a light brown crystalline residue, which was suspended in aqueous H$_2$O$_2$ (4 ml, 40 mmol, 30 w %), the suspension was stirred at 70° C. for 1 h. After cooling to ambient temperature the suspension was filtered. The remaining solid was washed two times with water and extracted with 15 ml of CH$_2$Cl$_2$. The organic layer was dried over MgSO$_4$ and filtered.

After removing the solvent in vacuo a white solid substance was obtained which was washed three times with 5 ml of diethyl ether. The product was dried at 50° C. in vacuum to yield 1.063 g (84%, 3.03 mmol) of compound of formula (1).

C/H/N-Analysis calc. % (found): C 65.14 (65.49), H 10.36 (10.51), N 15.99 (16.29)

$^1$H NMR (25° C., CD$_3$CN, 300.13 MHz, delta in ppm): 0.97 (t, 12H, CH$_3$), 1.35 (m, 8H, CH$_3$—CH$_2$), 1.61 (m, 8H, CH$_2$—CH$_2$N), 3.09 (m, 8H, NCH$_2$)

$^{13}$C NMR (25° C., CD$_3$CN, 300.13 MHz, delta in ppm): 13.87 (s, 4C, CH$_3$), 20.36 (t, 4C, CH$_2$—CH$_3$), 24.35 (s, 4C, N—CH$_2$—CH$_2$), 59.40 (t, 4C, NCH$_2$), 127.92 (dq, 3C, BF(CN)$_3$, $^1$J($^{13}$C-$^{11}$B)=75 Hz, $^2$J($^{13}$C-$^{19}$F)=37 Hz)

$^{11}$B NMR (25° C., CD$_3$CN, 96.29 MHz, delta in ppm): −17.86 (d, 1B, BF(CN)$_3$)

$^{19}$F NMR (25° C., CD$_3$CN, 300.13 MHz, delta in ppm): −211.68 (q, F, BF(CN)$_3$)

Example 4

EMIm[BF$_4$] (0.739 g, 3.73 mmol), prepared according to Preparation Description B, [Ph$_3$C][BF$_4$] (3.4 mol %, the mol % being based on the combined molar amount of [EMIm][BF$_4$] and [Ph$_3$C][BF$_4$], 43 mg) and (CH$_3$)$_3$SiCN (3.67 g, 37 mmol) were stirred under argon atmosphere at ambient temperatures for 20 h. The excess (CH$_3$)$_3$SiCN and any (CH$_3$)$_3$SiF were removed in vacuo resulting in a light brown oily residue, which was suspended in aqueous H$_2$O$_2$ (4 ml, 40 mmol, 30 w %), the suspension was stirred at 70° C. for 1 h. After cooling to ambient temperature 20 ml butyl acetate was added to the H$_2$O$_2$ solution. The resulting mixing was transferred into centrifuge tubes. After centrifugation (2000 rpm, 2 minutes) the supernatant layer was separated. The butyl acetate was removed on a rotary evaporator.

The obtained light yellow oil was washed three times with 5 ml of diethyl ether. After drying at 70° C. in vacuo 0.694 g (85%, 3.17 mmol) of compound of formula (2) were obtained.

$^1$H NMR (25° C., CD$_3$CN, 300.13 MHz, delta in ppm): 1.46 (t, 3H, CH$_3$), 3.82 (s, 3H, NCH$_3$), 4.16 (q, 2H, CH$_2$), 7.32 (m, 1H, EtNCH), 7.38 (m, 1H, MeNCH), 8.40 (s, 1H, NCHN)

$^{11}$B NMR (25° C., CD$_3$CN, 96.29 MHz, delta in ppm): −17.88 (d, 1B, BF(CN)$_3$)

$^{19}$F NMR (25° C., CD$_3$CN, 300.13 MHz, delta in ppm): −211.64 (q, 4F, BF(CN)$_3$)

Example 5

[(n-Bu)$_4$N][BF(CN)$_3$] (0.734 g, 2.10 mmol), prepared according to example 3, and [Ph$_3$C][BF$_4$] (86 mg, 11 mol %, the mol % being based on the combined molar amount of [(n-Bu)$_4$N][BF$_4$] and [Ph$_3$C][BF$_4$]) were dissolved in TMSCN (3.12 g, 31.4 mmol). After Tx hours of stirring at ambient temperature a $^{11}$B NMR and spectrum of the reaction mixture was measured and [Ph$_3$C][BF$_4$] was added, in order to have a desired mol % of [Ph$_3$C][BF$_4$]. Table 1 shows the details, Tx and the percentage of [BF(CN)$_3$]$^-$ and [B(CN)$_4$]$^-$ in the reaction mixture according to the NMR spectra.

TABLE 1

| Tx [h] | [Ph$_3$C][BF$_4$] Desired [mol %] | [Ph$_3$C][BF$_4$] Added [mg] | [BF(CN)$_3$]$^-$ [%] | [B(CN)$_4$]$^-$ [%] |
|---|---|---|---|---|
| 0 | 11 | 86 | — | — |
| 20 | 17 | 56 | 89 | 11 |
| 40 | 33 | 198 | 80 | 20 |
| 88 | — | — | 0 | 100 |

$^{11}$B NMR (25° C., CD$_3$CN, 96.29 MHz, delta in ppm): −17.88 (d, 1B, BF(CN)$_3$), −38.59 (s, 1B, B (CN)$_4$)

Example 8

[(n-Bu)$_4$N][BF$_4$] (0.491 g, 1.49 mmol), prepared according to Preparation Description A, FeCl$_3$ (20 mg, 7 mol %, the mol % being based on the combined molar amount of [(n-Bu)$_4$N][BF$_4$] and FeCl$_3$) and (CH$_3$)$_3$SiCN (1.58 g, 1.59 mmol) were stirred under argon atmosphere at ambient temperature for 3 h.

After the stirring at ambient temperature for 3 h an $^{11}$B and $^{19}$F NMR spectra were measured. In accordance to $^{19}$F NMR and $^{11}$B NMR the product contained 100% of compound of formula (4).

After removing the solvent the obtained light yellow solid substance was dried at 50° C. in vacuo to yield 0.400 g (69%, 1.17 mmol) of compound of formula (4).

C/H/N Analysis calc. % (found): C 62.97 (62.58), H 10.57 (10.65), N 12.24 (12.35)

$^1$H NMR (25° C., CDCl$_3$, 300.13 MHz, delta in ppm): 0.99 (t, 12H, CH$_3$), 1.41 (m, 8H, CH$_3$—CH$_2$), 1.61 (m, 8H, CH$_2$—CH$_2$N), 3.13 (m, 8H, NCH$_2$)

$^{11}$B NMR (25° C., CDCl$_3$, 300.13 MHz, delta in ppm): −7.2 (q, 1B, BF$_2$(CN)$_2$, $^1$J($^{11}$B-$^{19}$F)=42 Hz)

$^{13}$C NMR (25° C., CDCl$_3$, 300.13 MHz, delta in ppm): 13.3 (s, 4C, CH$_3$), 19.4 (t, 4C, CH$_2$—CH$_3$), 23.6 (s, 4C, N—CH$_2$—CH$_2$), 58.6 (t, 4C, NCH$_2$)

$^{19}$F NMR (25° C., CDCl$_3$, 300.13 MHz, delta in ppm): −153.1 (q, 2F, BF$_2$(CN)$_2$, $^1$J($^{11}$B-$^{19}$F)=42 Hz)

IR (ATR, 32 scans, v in cm$^{-1}$): 2966 (m), 2939 (m), 2878 (m), 2210 (m), 1474 (m), 1383 (m), 1242 (w), 1170 (w), 1006 (m), 1050 (s), 1007 (s), 939 (m), 880 (s), 797 (m), 737 (m), 632 (w), 550 (w)

Example 9

Example 8 was repeated with the differences:
1. MnCl$_2$ (9 mg, 5 mol %, the mol % being based on the combined molar amount of [(n-Bu)$_4$N][BF$_4$] and MnCl$_2$) were used instead of FeCl$_3$.
2. The reaction mixture was stirred for 20 h at ambient temperature instead of 3 h.

After the stirring for 20 h an $^{11}$B and $^{19}$F NMR spectra were measured. In accordance to $^{19}$F NMR and $^{11}$B NMR the product contained 100% of compound of formula (4).
NMR data was the same as in example 8.

Example 10

Example 8 was repeated with the difference:
1. PCl$_5$ (30 mg, 6 mol %, the mol % being based on the combined molar amount of [(n-Bu)$_4$N][BF$_4$] and PCl$_5$) were used instead of FeCl$_3$.

After the stirring for 3 h an $^{11}$B and $^{19}$F NMR spectra were measured. In accordance to $^{19}$F NMR and $^{11}$B NMR the product contained 100% of compound of formula (1).
After removing the solvent the obtained white solid substance was dried at 50° C. in vacuo to yield 0.680 g (90%, 1.66 mmol) of compound of formula (1).

C/H/N Analysis calc. % (found): C 65.14 (64.44), H 10.36 (10.41), N 15.99 (16.20)

$^1$H NMR (25° C., CDCl$_3$, 300.13 MHz, delta in ppm): 1.00 (t, 12H, CH$_3$), 1.41 (m, 8H, CH$_3$—CH$_2$), 1.60 (m, 8H, CH$_2$—CH$_2$N), 3.12 (m, 8H, NCH$_2$)

$^{11}$B NMR (25° C., CDCl$_3$, 300.13 MHz, delta in ppm): −17.6 (d, 1B, BF(CN)$_3$, $^1$J($^{11}$B-$^{19}$F)=45 Hz)

$^{13}$C NMR (25° C., CDCl$_3$, 300.13 MHz, delta in ppm): 13.3 (s, 4C, CH$_3$), 19.4 (t, 4C, CH$_2$—CH$_3$), 23.6 (s, 4C, N—CH$_2$—CH$_2$), 58.7 (t, 4C, NCH$_2$), 127.2 (dq, 3C, BF(CN)$_3$, $_1$J($^{13}$C-$^{19}$F)=38 Hz, $^1$J($^{13}$C-$^{11}$B)=75 Hz)

$^{19}$F NMR (25° C., CDCl$_3$, 300.13 MHz, delta in ppm): −210.9 (q, 1F, BF(CN)$_3$, $^1$J($^{11}$B-$^{19}$F)=45 Hz)

IR (ATR, 32 scans, v in cm$^{-1}$): 2964 (m), 2935 (m), 2876 (m), 2214 (w), 1474 (m), 1381 (m), 1171 (w), 1040 (m), 960 (w), 938 (,), 903 (s), 803 (w), 736 (m), 536 (w)

Example 11

Example 8 was repeated with the difference:
1. GaCl$_3$ (30 mg, 5 mol %, the mol % being based on the combined molar amount of [(n-Bu)$_4$N][BF$_4$] and GaCl$_3$) were used instead of FeCl$_3$.
2. The reaction mixture was stirred longer then 3 h.

After stirring for 3 h an $^{11}$B and $^{19}$F NMR spectra were measured. In accordance to $^{19}$F NMR and $^{11}$B NMR the product contained 99.9% of compound of formula (1).
NMR data was the same as in example 10.
After further stirring for additional 41 h another $^{11}$B NMR spectra was measured. In accordance to $^{11}$B NMR the reaction mixture contained 93.1% of compound of formula (1) and 6.9% of compound of formula (5).
NMR data was the same as in example 5.

Example 12

Example 8 was repeated with the difference:
1. TiCl$_4$ (0.01 ml, 5 mol %, the mol % being based on the combined molar amount of [(n-Bu)$_4$N][BF$_4$] and TiCl$_4$) were used instead of FeCl$_3$.

After the stirring for 3 h an $^{11}$B and $^{19}$F NMR spectra were measured. In accordance to $^{19}$F NMR and $^{11}$B NMR the product contained 100% of compound of formula (1).
NMR data was the same as in example 10.

Example 13

Example 8 was repeated with the differences:
1. CrCl$_3$ (14 mg, 5 mol %, the mol % being based on the combined molar amount of [(n-Bu)$_4$N][BF$_4$] and CrCl$_3$) were used instead of FeCl$_3$.
2. The reaction mixture was stirred for 25 h at ambient temperature instead of 3 h.

After the stirring for 25 h an $^{11}$B and $^{19}$F NMR spectra were measured. In accordance to $^{19}$F NMR and $^{11}$B NMR the product contained 100% of compound of formula (4).
NMR data was the same as in example 8.

Example 15

Example 8 was repeated with the difference:
1. NbCl$_5$ (20 mg, 5 mol %, the mol % being based on the combined molar amount of [(n-Bu)$_4$N][BF$_4$] and NbCl$_5$) were used instead of FeCl$_3$.

After the stirring for 3 h an $^{11}$B and $^{19}$F NMR spectra were measured. In accordance to $^{11}$B and $^{19}$F NMR the reaction mixture contained 100% of compound of formula (4).
After further stirring at ambient temperature in addition for 142 h again an $^{11}$B and $^{19}$F NMR were measured. In accordance to $^{11}$B and $^{19}$F NMR the reaction mixture contained 56% of compound of formula (4) and 44% of compound of formula (1).
NMR data was the same as in example 8 and 3.

Example 16

Example 8 was repeated with the difference:
1. SiCl$_4$ (0.01 ml, 5 mol %, the mol % being based on the combined molar amount of [(n-Bu)$_4$N][BF$_4$] and SiCl$_4$) were used instead of FeCl$_3$.

After the stirring for 3 h an $^{11}$B and $^{19}$F NMR spectra were measured. In accordance to $^{11}$B and $^{19}$F NMR the reaction mixture contained 100% of compound of formula (4).
NMR data was the same as in example 8.

Example 17

Example 8 was repeated with the difference:
1. GaCl$_3$ (30 mg, 5 mol %, the mol % being based on the combined molar amount of [(n-Bu)$_4$N][BF$_4$] and GaCl$_3$) were used instead of FeCl$_3$.
2. The reaction mixture was refluxed instead of stirring at ambient temperature.

After the stirring for 3 h an $^{11}$B and $^{19}$F NMR spectra were measured. In accordance to $^{11}$B the reaction mixture contained 100% of compound of formula (5).

After removing the solvent the obtained light yellow solid substance was dried at 50° C. in vacuo to yield 0.425 g (79%, 1.19 mmol) of compound of formula (5).

C/H/N Analysis calc. % (found): C 67.22 (66.43), H 10.15 (9.96), N 19.60 (19.00)

$^1$H NMR (25° C., CDCl$_3$, 300.13 MHz, delta in ppm): 1.03 (t, 12H, CH$_3$), 1.44 (m, 8H, CH$_3$—CH$_2$), 1.62 (m, 8H, CH$_2$—CH$_2$N), 3.12 (m, 8H, NCH$_2$)

$^{11}$B NMR (25° C., CDCl$_3$, 300.13 MHz, delta in ppm): −38.2 (s, 1B, B(CN)$_4$, $^1$J($^{11}$B-$^{19}$F)=71 Hz)

$^{13}$C NMR (25° C., CDCl$_3$, 300.13 MHz, delta in ppm): 13.5 (s, 4C, CH$_3$), 19.5 (t, 4C, CH$_2$—CH$_3$), 23.6 (s, 4C, N—CH$_2$—CH$_2$), 58.7 (t, 4C, NCH$_2$), 122.5 (q/sept, 4C, B(CN)$_4$, $^1$J($^{11}$B-$^{13}$C)=71 Hz, $^1$J($^{10}$B-$^{13}$C)=23 Hz)

IR (ATR, 32 scans, v in cm$^{-1}$): 2964 (m), 2935 (m), 2877 (m), 2214 (w), 1474 (m), 1381 (m), 1168 (w), 1110 (w), 1061 (w), 1035 (w), 991 (m), 967 (m), 931 (s), 886 (m), 802 (w), 735 (m), 535 (w)

Example 18

K[BF$_4$] (0.67 g, 5.32 mmol), GaCl$_3$ 6 mol %, the mol % being based on the combined molar amount of [(n-Bu)$_4$N][BF$_4$] and GaCl$_3$, 63 mg) and (CH$_3$)$_3$SiCN (5.8 g, 58.9 mmol) were stirred at ambient temperature for 15 h. Then a $^{11}$B NMR spectrum of the reaction mixture was measured. In accordance to $^{11}$B NMR the reaction mixture contained 93% of compound of formula (6) and 7% of K[BF$_4$].

Then the reaction mixture was refluxed for 9 h and a $^{11}$B NMR spectrum was measured. In accordance to $^{11}$B NMR the reaction mixture contained 95% of compound of formula (6) and 5% of compound of formula (7).

Example 20

Example 8 was repeated with the differences:
1. P(CN)$_3$ (17 mg, 5 mol %, the mol % being based on the combined molar amount of [(n-Bu)$_4$N][BF$_4$] and P(CN)$_3$) were used instead of FeCl$_3$.
2. The reaction mixture was stirred for 100 h at ambient temperature instead of 3 h.

After stirring at ambient temperature for 100 h an $^{11}$B and $^{19}$F NMR spectra were measured. In accordance to $^{19}$F and $^{11}$B NMR the product contained about 95.5% of compound of formula (4) and 4.5% of compound of formula (1).

NMR data was the same as in example 8.

Example 21

Example 17 was repeated with the differences:
1. 1-Butyl-3-methylimidazolium tetrafluoroborate (1.05 g, 4.65 mmol) were used instead of [(n-Bu)$_4$][BF$_4$].
2. The reaction mixture was stirred for 2 h at reflux temperature instead of 3 h.

After the stirring for 2 h an $^{11}$B and $^{19}$F NMR spectra were measured. In accordance to $^{19}$F and $^{11}$B NMR the product contained 100% of compound of formula (8).

The excess (CH$_3$)$_3$SiCN and any (CH$_3$)$_3$SiF were removed in vacuo resulting in a dark brown oily residue, which was suspended in aqueous H$_2$O$_2$ (7 ml, 70 mmol, 30 w %), the solution was stirred at 90° C. for 1 h. After cooling to ambient temperature 50 ml butyl acetate was added to the H$_2$O$_2$ solution. The resulting mixing was transferred into centrifuge tubes. After centrifugation (2000 rpm, 2 minutes) the supernatant layer was separated. The butyl acetate was removed on a rotary evaporator.

After drying at 100° C. in vacuo 1.00 g (85%, 3.95 mmol) of compound of formula (8) were obtained.

$^1$H NMR (25° C., CD$_3$CN, 250.13 MHz, delta in ppm): 0.97 (t, 3H, CH$_2$—CH$_3$), 1.37 (m, 2H, CH$_2$—CH$_3$), 1.87 (m, 2H, CH$_2$—CH$_2$), 3.94 (s, 3H, NCH$_3$), 4.17 (t, 2H, NCH$_2$), 7.33 (s, 1H, BuNCH), 7.34 (s, 1H, MeNCH), 8.44 (s, 1H, NCHN)

$^{11}$B NMR (25° C., CDCl$_3$, 80.25 MHz, delta in ppm): −38.4 (s, 1B, B(CN)$_4$, $^1$J($^{11}$B-$^{19}$F)=71 Hz)

$^{13}$C NMR (25° C., CD$_3$CN, 250.13 MHz, delta in ppm): 13.07 (s, 1C, CH$_3$), 19.15 (s, 1C, CH$_2$—CH$_3$), 31.56 (s, 1C, CH$_2$—CH$_2$), 36.39 (s, 1C, NCH$_3$), 49.94 (s, 1C, NCH$_2$), 122.3 (q+sep, 4C, B(CN)$_4$, $^1$J($^{11}$B-$^{13}$C)=71 Hz, $^1$J($^{10}$B-$^{13}$C)=24 Hz), 122.5 (s, 1C, BuNCH), 123.7 (s, 1C, MeNCH), 135.0 (s, 1C, NCHN)

Table 3

Tabel 3 gives an overview of some of the examples and their results, where the reaction has been done at ambient temperature.

Ex example m m as in formula (I)

t1 reaction time of reaction (Real)

[%] is the crude yield according to $^{19}$F NMR, except for those examples marked with (*), in the reaction mixture before any isolation or purification (*) in case of the examples marked with (*) the crude yield is according to $^{11}$B NMR instead of $^{19}$F NMR

TABLE 3

| | | | m | | | | |
|---|---|---|---|---|---|---|---|
| Ex | CAT | t1 [h] | 0 [%] | 1 [%] | 2 [%] | 3 [%] | 4 [%] |
| 11 (*) | GaCl$_3$ | 44 | — | — | — | 93.1 | 6.9 |
| 12 | TiCl$_4$ | 3 | — | — | — | 100 | — |
| 10 | PCl$_5$ | 3 | — | — | — | 100 | — |
| 20 | P(CN)$_3$ | 100 | — | — | 95.5 | 4.5 | — |
| 16 | SiCl$_4$ | 3 | — | — | 100 | — | — |
| 8 | FeCl$_3$ | 3 | — | — | 100 | — | — |
| 15 | NbCl$_5$ | 3 | — | — | 100 | — | — |
| 9 | MnCl$_2$ | 20 | — | — | 100 | — | — |
| 13 | CrCl$_3$ | 25 | — | — | 100 | — | — |

Table 4

Tabel 4 gives an overview of some of the examples and their results, where the reaction has been done at reflux temperature, which was ca. 125° C.

Ex example m m as in formula (I)

t1 reaction time of reaction (Real)

[%] is the crude yield according to $^{19}$F NMR, except for those examples marked with (*), in the reaction mixture before any isolation or purification (*) in case of the examples marked with (*) the crude yield is according to $^{11}$B NMR instead of $^{19}$F NMR

TABLE 4

| Ex | CAT | t1 [h] | m 0 [%] | 1 [%] | 2 [%] | 3 [%] | 4 [%] |
|---|---|---|---|---|---|---|---|
| 17 (*) | GaCl$_3$ | 3 | — | — | — | — | 100 |
| 21 (*) | GaCl$_3$ | 2 | — | — | — | — | 100 |

Comparative Example 1

No CATLEWISACID

Example 8 was repeated with the differences:
1. That no FeCl$_3$ was added to the reaction mixture.
2. The reaction mixture was stirred for 100 h instead of 3 h.

After stirring at ambient temperature for 100 h an $^{11}$B and $^{19}$F NMR spectra were measured. In accordance to $^{19}$F and $^{11}$B NMR the product contained about 82% of compound of formula (3) and 18% of compound of formula (4).
NMR data are the same as stated here:
$^1$H NMR (25° C., CDCl$_3$, 300.13 MHz, delta in ppm): 0.98 (t, 12H, CH$_3$), 1.41 (m, 8H, CH$_3$—CH$_2$), 1.61 (m, 8H, CH$_2$—CH$_2$N), 3.16 (m, 8H, NCH$_2$)
$^{11}$B NMR (25° C., CDCl$_3$, 300.13 MHz, delta in ppm): −3.6 (q, 1B, BF$_3$(CN), $^1$J($^{11}$B-$^{19}$F)=28 Hz)
$^{13}$C NMR (25° C., CDCl$_3$, 300.13 MHz, delta in ppm): 13.4 (s, 4C, CH$_3$), 19.5 (t, 4C, CH$_2$—CH$_3$), 23.7 (s, 4C, N—CH$_2$—CH$_2$), 58.5 (t, 4C, NCH$_2$)
$^{19}$F NMR (25° C., CDCl$_3$, 300.13 MHz, delta in ppm): −137.0 (q, 3F, BF$_3$(CN), $^1$J($^{11}$B-$^{19}$F)=28 Hz)
IR (ATR, 32 scans, v in cm$^{-1}$): 2964 (m), 2937 (m), 2877 (m), 2206 (w), 1474 (m), 1383 (m), 1261 (w), 1106 (s), 1058 (s), 990 (m), 952 (s), 881 (m), 799 (m), 738 (m), 681 (m), 532 (w)
and as in example 8.

Example 22

Example 8 was repeated with the differences:
1. Montmorillonit K10 (available at Sigma Aldrich, CAS Number 1318-93-0) (16 mg) was used instead of FeCl$_3$.
2. The reaction mixture was stirred for 146 h at ambient temperature instead of 3 h.

After the stirring for 146 h an $^{11}$B and $^{19}$F NMR spectra were measured. In accordance to $^{19}$F NMR and $^{11}$B NMR the product contained 100% of compound of formula (4).
NMR data was the same as in example 8.

Example 23

MCM-41 (mesostructured silica, available at Sigma Aldrich, CAS Number 7631-86-9) (0.93 g) and GaCl$_3$ (0.38 g) were stirred in benzene (10 ml) for 3 h at ambient temperature, then the reaction suspension was filtered, the residue was washed with benzene (10 ml), then the residue was dried in vacuo at 80° C. to provide a GaCl$_3$ catalyst supported on MCM-41.

Example 24

[(n-Bu)$_4$N][BF$_4$] (0.351 g, 1.07 mmol), prepared according to Preparation Description A, the GaCl$_3$ catalyst supported on MCM-41, prepared according to example 23, (7 mg) and (CH$_3$)$_3$SiCN (1.01 g, 10.4 mmol) were stirred under argon atmosphere at ambient temperature for 26 h.
After the stirring for 26 h an $^{11}$B and $^{19}$F NMR spectra were measured. In accordance to $^{19}$F NMR and $^{11}$B NMR the product contained 100% of compound of formula (1).
NMR data was the same as in example 10.

Example 25

SBA-15 (mesostructured silica, available at Sigma Aldrich, CAS Number 7631-86-9) (0.76 g) and GaCl$_3$ (0.44 g) were stirred in benzene (10 ml) for 3 h at ambient temperature, then the reaction suspension was filtered, the residue was washed with benzene (10 ml), then the residue was dried in vacuo at 80° C. to provide a GaCl$_3$ catalyst supported on SBA-15.

Example 26

[(n-Bu)$_4$N][BF$_4$] (0.366 g, 1.11 mmol), prepared according to Preparation Description A, the GaCl$_3$ catalyst supported on SBA-15, prepared according to example 25, (7 mg) and (CH$_3$)$_3$SiCN (1.09 g, 11.1 mmol) were stirred under argon atmosphere at ambient temperature for 26 h.
After the stirring for 26 h an $^{11}$B and $^{19}$F NMR spectra were measured. In accordance to $^{19}$F NMR and $^{11}$B NMR the product contained 100% of compound of formula (1).
NMR data was the same as in example 10.

Example 27

Li[BF$_4$] (0.474 g, 5.06 mmol), GaCl$_3$ (61 mg, 0.35 mmol, 6 mol %, the mol % being based on the combined molar amount of Li[BF$_4$] and GaCl$_3$) and (CH$_3$)$_3$SiCN (4.98 g, 50 mmol) were refluxed for 10 hours. Then a $^{11}$B NMR spectrum of the reaction mixture was measured. In accordance to $^{11}$B NMR the reaction mixture contained 22% of compound of formula (9) and 78% of compound of formula (10).
$^{11}$B NMR (25° C., D$_2$O, 80.25 MHz, delta in ppm): −17.8 (d, 1B, BF(CN)$_3$, $^1$J($^{11}$B-$^{19}$F)=43 Hz), −38.3 (s, 1B, B(CN)$_4$)

The invention claimed is:
1. A method for the preparation of a compound of formula (I);

the method comprises a step (St1);
step (St1) comprises a reaction (Rea1), wherein a compound of formula (A1) is reacted with trimethylsilylcyanide in the presence of CATLEWISACID;

CATLEWISACID is a catalyst CAT;
CAT is selected from the group consisting of [(CH$_3$)$_3$SiFSi(CH$_3$)$_3$][ANIO], Q1(R27)$_3$, guanidinium[ANIO], (R26)$_3$C[ANIO], adamantyl[ANIO], [(R24)$_3$O][ANIO], [(R25)$_3$Si][ANIO], Q2(R36)(R28)$_3$, Q3(R29)$_3$, Q4(R30)$_5$, Q5(R32)$_3$, Q6(R33)$_2$, Q8(R34)$_2$, Q9(R35)$_3$, Q10(R37)$_2$, zeolite and mixtures thereof;
ANIO is selected from the group consisting of [P(R40)$_{6-m1}$(R41)$_{m1}$]$^-$, [B(R42)$_{4-m2}$(R43)$_{m2}$]$^-$, F$^-$, Cl$^-$, Br$^-$, I$^-$, CN$^-$ and SCN$^-$;
R40 and R41 are identical of different in independently from each other selected from the group consisting of CN, SCN, F, Cl, Br and I;
m1 is 0, 1, 2, 3, 4 or 5;

R42 and R43 are identical of different in independently from each other selected from the group consisting of $C_6F_5$, CN, SCN, F, Cl, Br and I;

m2 is 0, 1, 2 or 3;

Q1 is selected from the group consisting of B, Al and Ga;

R27 is selected from the group consisting of $C_{1-10}$ alkoxy, halogen, $C_{1-10}$ alkyl, CN, SCN and $C_6F_5$;

R24 is $C_{1-10}$ alkyl;

R25 is $C_{1-10}$ alkyl;

R26 is selected from the group consisting of CN, SCN, Ph and $C_{1-10}$ alkyl;

Q2 is selected from the group consisting of Si and Ti;

R28 and R36 are identical or different and independently from each other selected from the group consisting of $C_{1-10}$ alkoxy, halogen, $C_{1-10}$ alkyl, CN, SCN and $C_6F_5$;

Q3 is selected from the group consisting of P, Sb and Bi;

R29 is selected from the group consisting of $C_{1-10}$ alkoxy, halogen, CN, SCN, $C_{1-10}$ alkyl and $C_6F_5$;

Q4 is selected from the group consisting of P, Sb and Nb;

R30 is selected from the group consisting of $C_{1-10}$ alkoxy, halogen, CN, SCN, $C_{1-10}$ alkyl and $C_6F_5$;

Q5 is selected from the group consisting of Cr and Fe;

R32 is selected from the group consisting of halogen, CN and SCN;

Q6 is selected from the group consisting of Mn, Fe, Pd and Pt;

R33 is selected from the group consisting of halogen, CN and SCN;

Q8 is selected from the group consisting of Cu, Zn, Cd and Hg;

R34 is selected from the group consisting of halogen, CN, and SCN;

Q9 Sc or Ln;

R35 is selected from the group consisting of halogen, CN, and SCN;

Q10 Ca;

R37 is halogen;

$Z^1$ is selected from the group consisting of B, Al, Ga, In and Tl;

m is 1, 2, 3 or 4;

n is 1, 2, 3 or 4;

$Cat^{n+}$ is selected from the group consisting of inorganic cation $CatINORG^{n+}$ and organic cation $CatORG^{n+}$;

$CatINORG^{n+}$ is a cation selected from the 1., 2., 3., 4., 5., 6., 7., 8., 9., 10., 11., 12., 13., 14., 15., or 16. group of the periodic table, or is a cation from the lanthanides or is a cation from the actinides or is $NH_4^+$;

$CatORG^{n+}$ is selected from the group consisting of $CatORG\text{-}A^+$, $CatORG\text{-}B^+$, $CatORG\text{-}C^+$, $[(CH_3)_3SiFSi(CH_3)_3]^+$, $Ph_3C^+$, guanidinium and $(H_2(R18)N\text{-}R16\text{-}N(R19)H_2)^{2+}$;

$CatORG\text{-}A^+$ is $(WR2R3R4R5)^+$, wherein

W is a nitrogen or phosphorus; and (i) R2, R3, R4 and R5 are identical or different and independently from each other selected from the group consisting of H, $C_{1-20}$ alkyl, $C_{1-20}$ perfluoroalkyl, $C_{3-10}$ cycloalkyl and $C_{6-10}$ aryl, with the proviso, that at least one of the residues R2, R3, R4 and R5 is not H; or (ii) R2 and R3 together are a hydrocarbon chain and form together with W a 5- to 7-membered saturated or unsaturated heterocyclic ring, R4 and R5 are identical or different and independently from each other selected from the group consisting of H, $C_{1-20}$ alkyl, $C_{1-20}$ perfluoroalkyl, $C_{3-10}$ cycloalkyl and $C_{6-10}$ aryl; or (iii) R2 and R3 together are a hydrocarbon chain and form together with W, and R4 and R5 together are a hydrocarbon chain and form together with W, independently from each other, 5- to 7-membered saturated or unsaturated heterocyclic rings;

$CatORG\text{-}B^+$ is $(XR6R7R8)^+$, wherein

X is nitrogen,

R6 and R7 together are a hydrocarbon chain and form together with X a 5- to 7-membered unsaturated heterocyclic ring in which X is connected by a single bond and a double bond to R6 and R7 respectively, R8 is selected from the group consisting of H, $C_{1-20}$ alkyl, $C_{2-8}$ alkenyl, $C_{1-20}$ perfluoroalkyl, $C_{3-10}$ cycloalkyl or $C_{6-10}$ aryl;

$CatORG\text{-}C^+$ is $(YR9R10R11)^+$, wherein

Y is sulphur;

(i) R9, R10 and R11 are identical or different and independently from each other selected from the group consisting of H, $C_{1-20}$ alkyl, $C_{1-20}$ perfluoroalkyl, $C_{3-10}$ cycloalkyl and $C_{6-10}$ aryl; or (ii) R9 and R10 together are a hydrocarbon chain and form together with Y a 5- to 7-membered saturated or unsaturated ring, R11 is selected from the group consisting of H, $C_{1-20}$ alkyl, $C_{1-20}$ perfluoroalkyl, $C_{3-10}$ cycloalkyl and $C_{6-10}$ aryl;

the residues R2, R3, R4, R5, R6, R7, R8, R9, R10 and R11 are, independently from each other, unsubstituted or, where applicable, substituted by 1, 2, 3, 4, 5 or 6 substituents selected from the group consisting of $C_{1-4}$ alkyl, $C_{3-10}$ cycloalkyl, $C_{2-8}$ alkenyl, phenyl, benzyl, halogen, cyano and $C_{1-4}$ alkoxy;

in any of said hydrocarbon chains formed by R2 and R3, by R4 and R5, by R6 and R7, by R9 and R10, 1 or 2 carbon atoms of said hydrocarbon chains can be exchanged for 1 or 2 heteroatoms respectively, said one or two heteroatoms being selected from the group consisting of O, N and S; in case of an exchange for N, this N is unsubstituted or substituted by a residue selected from the group consisting of $C_{1-8}$ alkyl, $C_{3-10}$ cycloalkyl, $C_{2-8}$ alkenyl and $C_{1-8}$ perfluoroalkyl;

R16 is selected from the group consisting of $C_{2-8}$ alkylen, $C_{3-8}$ cycloalkylen, phenylen, C(H)(phenyl), R17(—O—R17)$_{n1}$;

R17 is selected from the group consisting of $CH_2$—$CH_2$, $CH_2$—$CH_2$—$CH_2$, $CH_2$—$C(H)(CH_3)$—$CH_2$, $CH_2$—$CH_2$—$C(H)(CH_3)$ and $CH_2$—$CH_2$—$CH_2$—$CH_2$;

R18 and R19 are identical or different and independently from each other selected from the group consisting of H, $C_{1-8}$ alkyl, $C_{3-8}$ cycloalkyl, phenyl and benzyl;

n1 is an integer from 1 to 20.

2. The method according to claim 1, wherein $Z^1$ is B.

3. The method according to claim 1, wherein n is 1 or 2.

4. The method according to claim 1, wherein m is 2, 3 or 4.

5. The method according to claim 1, wherein m is 3 or 4.

6. The method according to claim 1, wherein $CatINORG^{n+}$ is a cation selected from the 1., 2., 3., 4., 5., 6., 7., 8., 9., 10., 11., 12., 13., 14. or 15. group of the periodic table or is a cation from the lanthanides or is $NH_4^+$.

7. The method according to claim 1, wherein
CatORG$^{n+}$ is selected from the group consisting of ammonium, phosphonium, sulfonium, pyrrolidinium, pyrrolinium, pyrrolium, pyrazolium, pyrazolinium, imidazolium, imidazolinium, triazolium, oxazolium, thiazolium, piperidinium, piperazinium, morpholinium, pyridinium, pyridazinium, pyrimidinium, pyrazinium, 1,3-dioxolium, pyrylium, thiopyrylium, quinoxalinium, indolinium, indolium, [(CH$_3$)$_3$SiFSi(CH$_3$)$_3$]$^+$, Ph$_3$C$^+$, and mixtures thereof.

8. The method according to claim 1, wherein
CatORG$^{n+}$ is selected from the group consisting of

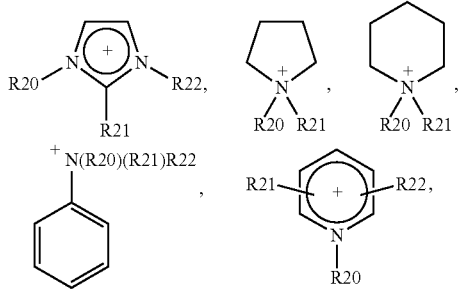

[N(R20)(R21)(R22)R23]$^+$, [P(R20)(R21)(R22)R23]$^+$, [(CH$_3$)$_3$SiFSi(CH$_3$)$_3$]$^+$, Ph$_3$C$^+$, and mixtures thereof;
wherein
R20, R21, R23 are identical or different and independently from each other selected from the group consisting of H, C$_{1-20}$ alkyl, C$_{3-10}$ cycloalkyl and allyl;
R22 is C$_{1-20}$ alkyl, C$_{3-10}$ cycloalkyl or allyl.

9. The method according to claim 1, wherein
compound of formula (I) is compound (Group-I),
compound (Group-I) is selected from the group consisting of compound of formula (Ia) and compound of formula (Ib);

[Cat$^{n+}$][(BF(CN)$_3$)$^-$]$_n$ (Ia)

[Cat$^{n+}$][(B(CN)$_4$)$^-$]$_n$ (Ib)

Cat$^+$ and n are as defined in claim 1.

10. The method according to claim 1, wherein
compound of formula (I) is compound (GROUP-II), compound (GROUP-II) is selected from the group consisting of K$^+$[BF(CN)$_3$)$^-$], Ag$^+$[(BF(CN)$_3$)$^-$], Li$^+$[(BF(CN)$_3$)$^-$], Mg$^{2+}$[(BF(CN3)$^-$]$_2$, Ca$^{2+}$[(BF(CN)$_3$)$^-$]$_2$, [N(n-Pr)$_4$]$^+$[(BF(CN)$_3$)$^-$], [N(n-Bu)$_4$]$^+$[(BF(CN)$_3$)$^-$], [P(n-Bu)$_4$]$^+$[(BF(CN)$_3$)$^-$], 1,3-dimethylimidazolium [(BF(CN)$_3$)$^-$], 1-ethyl-3-methylimidazolium [(BF(CN)$_3$)$^-$], 1-propyl-3-methylimidazolium [(BF(CN)$_3$)$^-$] and mixtures thereof.

11. The method according to claim 1, wherein
compound of formula (I) is compound (GROUP-III), compound (GROUP-III) is selected from the group consisting of K$^+$[((B(CN)$_4$)$^-$], Ag$^+$[((B(CN)$_4$)$^-$], Li$^+$[((B(CN)$_4$)$^-$], Mg$^{2+}$[(B(CN)$_4$)$^-$]$_2$, Ca$^{2+}$[(B(CN)$_4$)$^-$]$_2$, [N(n-Pr)$_4$]$^+$[(B(CN)$_4$)$^-$], [N(n-Bu)$_4$]$^+$[(B(CN)$_4$)$^-$], [P(n-Bu)$_4$]$^+$[(B(CN)$_4$)$^-$], 1,3-dimethylimidazolium [(B(CN)$_4$)$^-$], 1-ethyl-3-methylimidazolium [(B(CN)$_4$)$^-$], 1-propyl-3-methylimidazolium [(B(CN)$_4$)$^-$] and mixtures thereof.

12. The method according to claim 1, wherein
compound of formula (I) is compound (GROUP-IV), compound (GROUP-IV) is selected from the group consisting of K$^+$[((B(F)$_2$(CN)$_2$)$^-$], Ag$^+$[((B(F)$_2$(CN)$_2$)$^-$], Li$^+$[((B(F)$_2$(CN)$_2$)$^-$], Mg$^{2+}$[(B(F)$_2$(CN)$_2$)$^-$]$_2$, Ca$^{2+}$[(B(F)$_2$(CN)$_2$)$^-$]$_2$, [N(n-Pr)$_4$]$^+$[(B(F)$_2$(CN)$_2$)$^-$], [N(n-Bu)$_4$]$^+$[(B(F)$_2$(CN)$_2$)$^-$], [P(n-Bu)$_4$]$^+$[(B(F)$_2$(CN)$_2$)$^-$], 1,3-dimethylimidazolium [(B(F)$_2$(CN)$_2$)$^-$], 1-ethyl-3-methylimidazolium [(B(F)$_2$(CN)$_2$)$^+$], 1-propyl-3-methylimidazolium [(B(F)$_2$(CN)$_2$)$^-$] and mixtures thereof.

13. The method according to claim 1, wherein
compound of formula (I) is compound (GROUP-V), compound (GROUP-V) is selected from the group consisting of K$^+$[((B(F)$_3$(CN))$^-$], Ag$^+$[((B(F)$_3$(CN))$^-$], Li$^+$[((B(F)$_3$(CN))$^-$], Mg$^{2+}$[(B(F)$_3$(CN))$^-$]$_2$, Ca$^{2+}$[(B(F)$_3$(CN))$^-$]$_2$, [N(n-Pr)$_4$]$^+$[(B(F)$_3$(CN))$^-$], [N(n-Bu)$_4$]$^+$[(B(F)$_3$(CN))$^-$], [P(n-Bu)$_4$]$^+$[(B(F)$_3$(CN))$^-$], 1,3-dimethylimidazolium [(B(F)$_3$(CN))$^-$], 1-ethyl-3-methylimidazolium [(B(F)$_3$(CN))$^-$], 1-propyl-3-methylimidazolium [(B(F)$_3$(CN))$^-$] and mixtures thereof.

14. The method according to claim 1, wherein
compound of formula (I) is compound (GROUP), compound (GROUP) is selected from the group consisting of compound of formula (1), compound of formula (2), compound of formula (3), compound of formula (4), compound of formula (5), compound of formula (6), compound of formula (7), compound of formula (8), compound of formula (9), compound of formula (10), and mixtures thereof;

[(n-Bu)$_4$N][BF(CN)$_3$]        (1)

[EMIm][BF(CN)$_3$]        (2)

[(n-Bu)$_4$N][BF$_3$(CN)]        (3)

[(n-Bu)$_4$N][BF$_2$(CN)$_2$]        (4)

[(n-Bu)$_4$N][B(CN)$_4$]        (5)

K[BF(CN)$_3$]        (6)

K[B(CN)$_4$]        (7)

[BMIm][B(CN)$_4$]        (8)

Li[BF(CN)$_3$]        (9)

Li[B(CN)$_4$]        (10).

15. The method according to claim 1, wherein
the method comprises additionally to step (St1) a step (St2), step (St2) is done after step (St1);
step (St2) comprises a reaction (Rea2), reaction (Rea2) is a metathesis reaction wherein cation Cat$^{n+}$ in compound of formula (I) is exchanged for a cation different from Cat$^{n+}$;
compound of formula (I) having been prepared in step (St1);
Cat$^{n+}$, n, compound of formula (I) and step (St1) are as defined in claim 1.

16. The method according to claim 1, wherein
the method comprises additionally to step (St1) a step (St1-1), step (St1-1) is done after step (St1);
step (St1-1) comprises a reaction (Rea1-1), wherein compound of formula (I), obtained in step (1), is reacted with trimethylsilylcyanide.

17. The method according to claim 16, wherein
the reaction (Rea(1-1) is done in the presence of CATLEWISACID;
with CATLEWISACID as defined in claim 1.

18. A method for the preparation of a compound of formula (I);

$$[Cat^{n+}][(Z^1F_{4-m}(CN)_m)^-]_n \qquad (I)$$

the method comprises a step (St1);
step (St1) comprises a reaction (Rea1), wherein CATLEWISACID [$(Z^1F_4)^-$] is reacted with trimethylsilylcyanide in the presence of $Cat^{n+}$;
CATLEWISACID is selected from the group consisting of [$(CH_3)_3SiFSi(CH_3)_3$]$^+$, guanidinium, $(R26)_3C^+$, adamantyl cation, [$(R24)_3O$]$^+$, [$(R25)_3Si$]$^+$, and mixtures thereof;
R24 is $C_{1-10}$ alkyl;
R25 is $C_{1-10}$ alkyl;
R26 is selected from the group consisting of CN, SCN, Ph and $C_{1-10}$ alkyl;
$Z^1$ is selected from the group consisting of B, Al, Ga, In and Tl;
m is 1, 2, 3 or 4;
n is 1, 2, 3 or 4;
$Cat^{n+}$ is selected from the group consisting of inorganic cation $CatINORG^{n+}$ and organic cation $CatORG^{n+}$;
$CatINORG^{n+}$ is a cation selected from the 1., 2., 3., 4., 5., 6., 7., 8., 9., 10., 11., 12., 13., 14., 15. or 16. group of the periodic table, or is a cation from the lanthanides or is a cation from the actinides or is $NH_4^+$;
$CatORG^{n+}$ is selected from the group consisting of CatORG-A$^+$, CatORG-B$^+$, CatORG-C$^+$, [$(CH_3)_3SiFSi(CH_3)_3$]$^+$, $Ph_3C^+$, guanidinium and $(H_2(R18)N-R16-N(R19)H_2)^{2+}$;
CatORG-A$^+$ is $(WR2R3R4R5)^+$,
wherein
W is a nitrogen or phosphorus; and
(i) R2, R3, R4 and R5 are identical or different and independently from each other selected from the group consisting of H, $C_{1-20}$ alkyl, $C_{1-20}$ perfluoroalkyl, $C_{3-10}$ cycloalkyl and $C_{6-10}$ aryl, with the proviso, that at least one of the residues R2, R3, R4 and R5 is not H; or
(ii) R2 and R3 together are a hydrocarbon chain and form together with W a 5- to 7-membered saturated or unsaturated heterocyclic ring,
R4 and R5 are identical or different and independently from each other selected from the group consisting of H, $C_{1-20}$ alkyl, $C_{1-20}$ perfluoroalkyl, $C_{3-10}$ cycloalkyl and $C_{6-10}$ aryl; or
(iii) R2 and R3 together are a hydrocarbon chain and form together with W, and R4 and R5 together are a hydrocarbon chain and form together with W, independently from each other, 5- to 7-membered saturated or unsaturated heterocyclic rings;
CatORG-B$^+$ is $(XR6R7R8)^+$,
wherein
X is nitrogen,
R6 and R7 together are a hydrocarbon chain and form together with X a 5- to 7-membered unsaturated heterocyclic ring in which X is connected by a single bond and a double bond to R6 and R7 respectively,
R8 is selected from the group consisting of H, $C_{1-20}$ alkyl, $C_{2-8}$ alkenyl, $C_{1-20}$ perfluoroalkyl, $C_{3-10}$ cycloalkyl or $C_{6-10}$ aryl;
CatORG-C$^+$ is $(YR9R10R11)^+$,
wherein
Y is sulphur;
(i) R9, R10 and R11 are identical or different and independently from each other selected from the group consisting of H, $C_{1-20}$ alkyl, $C_{1-20}$ perfluoroalkyl, $C_{3-10}$ cycloalkyl and $C_{6-10}$ aryl; or
(ii) R9 and R10 together are a hydrocarbon chain and form together with Y a 5- to 7-membered saturated or unsaturated ring,
R11 is selected from the group consisting of H, $C_{1-20}$ alkyl, $C_{1-20}$ perfluoroalkyl, $C_{3-10}$ cycloalkyl and $C_{6-10}$ aryl;
the residues R2, R3, R4, R5, R6, R7, R8, R9, R10 and R11 are, independently from each other, unsubstituted or, where applicable, substituted by 1, 2, 3, 4, 5 or 6 substituents selected from the group consisting of $C_{1-4}$ alkyl, $C_{3-10}$ cycloalkyl, $C_{2-8}$ alkenyl, phenyl, benzyl, halogen, cyano and $C_{1-4}$ alkoxy;
in any of said hydrocarbon chains formed by R2 and R3, by R4 and R5, by R6 and R7, by R9 and R10, 1 or 2 carbon atoms of said hydrocarbon chains can be exchanged for 1 or 2 heteroatoms respectively, said one or two heteroatoms being selected from the group consisting of O, N and S; in case of an exchange for N, this N is unsubstituted or substituted by a residue selected from the group consisting of $C_{1-8}$ alkyl, $C_{3-10}$ cycloalkyl, $C_{2-8}$ alkenyl and $C_{1-8}$ perfluoroalkyl;
R16 is selected from the group consisting of $C_{2-8}$ alkylen, $C_{3-8}$ cycloalkylen, phenylen, C(H)(phenyl), R17(—O—R17)$_{n1}$;
R17 is selected from the group consisting of $CH_2$—$CH_2$, $CH_2$—$CH_2$—$CH_2$, $CH_2$—$C(H)(CH_3)$—$CH_2$, $CH_2$—$CH_2$—$C(H)(CH_3)$ and $CH_2$—$CH_2$—$CH_2$—$CH_2$;
R18 and R19 are identical or different and independently from each other selected from the group consisting of H, $C_{1-8}$ alkyl, $C_{3-8}$ cycloalkyl, phenyl and benzyl;
n1 is an integer from 1 to 20.

19. The method according to claim 18, wherein $Z^1$ is B.

20. The method according to claim 18, wherein n is 1 or 2.

21. The method according to claim 18, wherein CATLEWISACID is selected from the group consisting of [$(CH_3)_3SiFSi(CH_3)_3$]$^+$, guanidinium, $(R26)_3C^+$, [$(R24)_3O$]$^+$, [$(R25)_3Si$]$^+$, and mixtures thereof; with R24, R25 and R26 as defined in claim 18.

22. The method according to claim 18, wherein
R24 is $C_{1-4}$ alkyl;
R25 is $C_{1-7}$ alkyl;
R26 is selected from the group consisting of Ph and $C_{1-4}$ alkyl.

23. The method according to claim 18, wherein CATLEWISACID is selected from the group consisting of [$(CH_3)_3SiFSi(CH_3)_3$]$^+$, $(Ph)_3C^+$, $(CH)_3C^+$, [$(C_{1-3}$ alkyl)$_3O$]$^+$, [$(C_{1-4}$ alkyl)$_3Si$]$^+$, and mixtures thereof.

24. The method according to claim 18, wherein CATLEWISACID is selected from the group consisting of [$(CH_3)_3SiFSi(CH_3)_3$]$^+$, $Ph_3C^+$, [(ethyl)$_3Si$]$^+$, and mixtures thereof.

25. The method according to claim 18, wherein $Cat^{n+}$ is used in the reaction (Rea1) in form of a compound of formula (A1);

$$[Cat^{n+}][(Z^1F_4)^-]_n \qquad (A1)$$

wherein
$Cat^{n+}$, $Z^1$ and n are defined as in claim 18.

26. The method according to claim 18, wherein m is 2, 3 or 4.

27. The method according to claim 18, wherein m is 3 or 4.

28. The method according to claim 18, wherein CatINORG$^{n+}$ is a cation selected from the 1., 2., 3., 4., 5., 6., 7., 8., 9., 10., 11., 12., 13., 14. or 15. group of the periodic table or is a cation from the lanthanides or is NH$_4^+$.

29. The method according to claim 18, wherein CatORG$^{n+}$ is selected from the group consisting of ammonium, phosphonium, sulfonium, pyrrolidinium, pyrrolinium, pyrrolium, pyrazolium, pyrazolinium, imidazolium, imidazolinium, triazolium, oxazolium, thiazolium, piperidinium, piperazinium, morpholinium, pyridinium, pyridazinium, pyrimidinium, pyrazinium, 1,3-dioxolium, pyrylium, thiopyrylium, quinoxalinium, indolinium, indolium, [(CH$_3$)$_3$SiFSi(CH$_3$)$_3$]$^+$, Ph$_3$C$^+$, and mixtures thereof.

30. The method according to claim 18, wherein CatORG$^{n+}$ is selected from the group consisting of

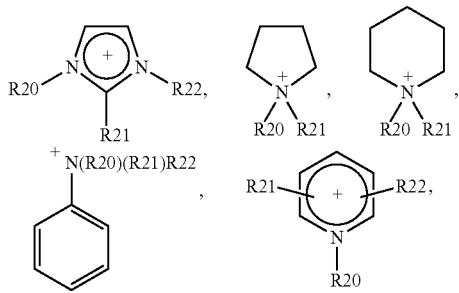

[N(R20)(R21)(R22)R23]$^+$, [P(R20)(R21)(R22)R23]$^+$, [(CH$_3$)$_3$SiFSi(CH$_3$)$_3$]$^+$, Ph$_3$C$^+$, and mixtures thereof; wherein
R20, R21, R23 are identical or different and independently from each other selected from the group consisting of H, C$_{1-20}$ alkyl, C$_{3-10}$ cycloalkyl and allyl;
R22 is C$_{1-20}$ alkyl, C$_{3-10}$ cycloalkyl or allyl.

31. The method according to claim 18, wherein compound of formula (I) is compound (Group-II), compound (Group-I) is selected from the group consisting of compound of formula (Ia) and compound of formula (Ib);

[Cat$^{n+}$][(BF(CN)$_3$)$^-$]$_n$ (Ia)

[Cat$^{n+}$][(B(CN)$_4$)$^-$]$_n$ (Ib)

Cat$^{n+}$ and n are as defined in claim 18.

32. The method according to claim 18, wherein compound of formula (I) is compound (GROUP-II), compound (GROUP-II) is selected from the group consisting of K$^+$[(BF(CN)$_3$)$^-$], Ag$^+$[(BF(CN)$_3$)$^-$], Li$^+$[(BF(CN)$_3$)$^-$], Mg$^{2+}$[(BF(CN3)$^-$]$_2$, Ca$^{2+}$[(BF(CN)$_3$)$^-$]$_2$, [N(n-Pr)$_4$]$^+$[(BF(CN)$_3$)$^-$], [N(n-Bu)$_4$]$^+$[(BF(CN)$_3$)$^-$], [P(n-Bu)$_4$]$^+$[(BF(CN)$_3$)$^-$], 1,3-dimethylimidazolium [(BF(CN)$_3$)$^-$], 1-ethyl-3-methylimidazolium [(BF(CN)$_3$)$^-$], 1-propyl-3-methylimidazolium [(BF(CN)$_3$)$^-$] and mixtures thereof.

33. The method according to claim 18, wherein compound of formula (I) is compound (GROUP-III), compound (GROUP-III) is selected from the group consisting of consisting of K$^+$[((B(CN)$_4$)$^-$], Ag$^+$[((B(CN)$_4$)$^-$], Li$^+$[((B(CN)$_4$)$^-$], Mg$^{2+}$[(B(CN)$_4$)$^-$]$_2$, Ca$^{2+}$[(B(CN)$_4$)$^-$]$_2$, [N(n-Pr)$_4$]$^+$[(B(CN)$_4$)$^-$], [N(n-Bu)$_4$]$^+$[(B(CN)$_4$)$^-$], [P(n-Bu)$_4$]$^+$[(B(CN)$_4$)$^-$], 1,3-dimethylimidazolium [(B(CN)$_4$)$^-$], 1-ethyl-3-methylimidazolium [(B(CN)$_4$)$^-$], 1-propyl-3-methylimidazolium [(B(CN)$_4$)$^-$] and mixtures thereof.

34. The method according to claim 18, wherein compound of formula (I) is compound (GROUP-IV), compound (GROUP-IV) is selected from the group consisting of K$^+$[((B(F)$_2$(CN)$_2$)$^-$], Ag$^+$[((B(F)$_2$(CN)$_2$)$^-$], Li$^+$[(B(F)$_2$(CN)$_2$)$^-$], Mg$^{2+}$[(B(F)$_2$(CN)$_2$)$^-$]$_2$, Ca$^{2+}$[(B(F)$_2$(CN)$_2$)$^-$]$_2$, [N(n-Pr)$_4$]$^+$[(B(F)$_2$(CN)$_2$)$^-$], [N(n-Bu)$_4$]$^+$[(B(F)$_2$(CN)$_2$)$^-$], [P(n-Bu)$_4$]$^+$[(B(F)$_2$(CN)$_2$)$^-$], 1,3-dimethylimidazolium [(B(F)$_2$(CN)$_2$)$^-$], 1-ethyl-3-methylimidazolium [(B(F)$_2$(CN)$_2$)$^+$], 1-propyl-3-methylimidazolium [(B(F)$_2$(CN)$_2$)$^-$] and mixtures thereof.

35. The method according to claim 18, wherein compound of formula (I) is compound (GROUP-V), compound (GROUP-V) is selected from the group consisting of K$^+$[((B(F)$_3$(CN))$^-$], Ag$^+$[((B(F)$_3$(CN))$^-$], Li$^+$[((B(F)$_3$(CN))$^-$], Mg$^{2+}$[(B(F)$_3$(CN))$^-$]$_2$, Ca$^{2+}$[(B(F)$_3$ (CN))$^-$]$_2$, [N(n-Pr)$_4$]$^+$[(B(F)$_3$(CN))$^-$], [N(n-Bu)$_4$]$^+$[(B(F)$_3$(CN))$^-$], [P(n-Bu)$_4$]$^+$[(B(F)$_3$(CN))$^-$], 1,3-dimethylimidazolium [(B(F)$_3$(CN))$^-$], 1-ethyl-3-methylimidazolium [(B(F)$_3$(CN))$^-$], 1-propyl-3-methylimidazolium [(B(F)$_3$(CN))$^-$] and mixtures thereof.

36. The method according to claim 18, wherein compound of formula (I) is compound (GROUP), compound (GROUP) is selected from the group consisting of compound of formula (1), compound of formula (2), compound of formula (3), compound of formula (4), compound of formula (5), compound of formula (6), compound of formula (7), compound of formula (8), compound of formula (9), compound of formula (10), and mixtures thereof;

[(n-Bu)$_4$N][BF(CN)$_3$] (1)

[EMIm][BF(CN)$_3$] (2)

[(n-Bu)$_4$N][BF$_3$(CN)] (3)

[(n-Bu)$_4$N][BF$_2$(CN)$_2$] (4)

[(n-Bu)$_4$N][B(CN)$_4$] (5)

K[BF(CN)$_3$] (6)

K[B(CN)$_4$] (7)

[BMIm][B(CN)$_4$] (8)

Li[BF(CN)$_3$] (9)

Li[B(CN)$_4$] (10).

37. The method according to claim 18, wherein the method comprises additionally to step (St1) a step (St2), step (St2) is done after step (St1);
step (St2) comprises a reaction (Rea2), reaction (Rea2) is a metathesis reaction wherein cation Cat$^{n+}$ in compound of formula (I) is exchanged for a cation different from Cat$^{n+}$;
compound of formula (I) having been prepared in step (St1);
Cat$^{n+}$, n, compound of formula (I) and step (St1) are as defined in claim 18.

38. The method according to claim 18, wherein the method comprises additionally to step (St1) a step (St1-1), step (St1-1) is done after step (St1);
step (St1-1) comprises a reaction. (Rea1-1), wherein compound of formula (I), obtained in step (1), is reacted with trimethylsilylcyanide.

* * * * *